United States Patent
Wang et al.

(10) Patent No.: US 10,647,767 B2
(45) Date of Patent: *May 12, 2020

(54) ANTI-GM-CSF ANTIBODIES AND USES THEREOF

(71) Applicant: I-Mab-Biopharma Co., Ltd., Pudong Shanghai (CN)

(72) Inventors: Zhengyi Wang, Shanghai (CN); Lei Fang, Shanghai (CN); Bingshi Guo, Shanghai (CN); Jingwu Zang, Shanghai (CN)

(73) Assignee: I-Mab Biopharma Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/744,734

(22) PCT Filed: Sep. 18, 2017

(86) PCT No.: PCT/CN2017/102057
§ 371 (c)(1),
(2) Date: Jan. 12, 2018

(87) PCT Pub. No.: WO2018/050111
PCT Pub. Date: Mar. 22, 2018

(65) Prior Publication Data
US 2019/0002549 A1      Jan. 3, 2019

(30) Foreign Application Priority Data

Sep. 19, 2016   (CN) .......................... 2016 1 0831525
Sep. 19, 2016   (CN) .......................... 2016 1 0832677

(51) Int. Cl.
| | |
|---|---|
| *A61K 39/00* | (2006.01) |
| *A61K 39/395* | (2006.01) |
| *C07K 16/24* | (2006.01) |
| *A61P 19/02* | (2006.01) |
| *A61P 29/00* | (2006.01) |
| *A61P 35/02* | (2006.01) |
| *A61P 37/02* | (2006.01) |
| *A61P 37/06* | (2006.01) |
| *A61P 35/00* | (2006.01) |
| *G01N 33/68* | (2006.01) |

(52) U.S. Cl.
CPC .......... *C07K 16/24* (2013.01); *A61K 39/3955* (2013.01); *A61P 19/02* (2018.01); *A61P 29/00* (2018.01); *A61P 35/00* (2018.01); *A61P 35/02* (2018.01); *A61P 37/02* (2018.01); *A61P 37/06* (2018.01); *C07K 16/243* (2013.01); *G01N 33/6863* (2013.01); *A61K 2039/505* (2013.01); *C07K 2317/24* (2013.01); *C07K 2317/30* (2013.01); *C07K 2317/33* (2013.01); *C07K 2317/73* (2013.01); *C07K 2317/76* (2013.01); *C07K 2317/92* (2013.01); *C07K 2317/94* (2013.01); *G01N 2333/535* (2013.01)

(58) Field of Classification Search
CPC .......... A61K 39/3955; A61K 2039/505; C07K 16/24; C07K 16/243; C07K 2317/24; C07K 2317/30; C07K 2317/33; C07K 2317/73; C07K 2317/76; C07K 2317/92; C07K 2317/96; A61P 35/02; A61P 19/02; A61P 29/00; A61P 37/02; A61P 37/06
See application file for complete search history.

(56) References Cited

U.S. PATENT DOCUMENTS

| | | | |
|---|---|---|---|
| 8,268,311 B2 | 9/2012 | Kirchner et al. | |
| 2010/0291075 A1* | 11/2010 | Chan-Hui | C07K 16/243 |
| | | | 424/133.1 |
| 2014/0065163 A1 | 3/2014 | Magnenat et al. | |

FOREIGN PATENT DOCUMENTS

| | | |
|---|---|---|
| EP | 2535353 | 12/2012 |
| WO | WO 2007/092939 | 8/2007 |
| WO | WO 2008/064321 | 5/2008 |
| WO | WO 2008/141391 | 11/2008 |
| WO | WO 2010/071923 | 7/2010 |
| WO | WO 2010/124163 | 10/2010 |
| WO | WO 2011/153592 | 12/2011 |
| WO | WO 2014/044768 | 3/2014 |
| WO | WO 2014/138862 | 9/2014 |
| WO | WO 2015/028657 | 3/2015 |

OTHER PUBLICATIONS

Bendig, M.M. Humanization of rodent monoclonal antibodies by CDR grafting. Methods: A Companion to Methods in Enzymology, 1995, vol. 8, p. 83-93.*
Casset, F., et al. A peptide mimetic of an anti-CD4 monoclonal antibody by rational design. Biochem. Biophys. Res. Comm., 2003, vol. 307, p. 198-205.*
MacCallum, R.M., et al. Antibody-antigen interactions: Contact analysis and binding site topography. J. Mol. Biol., 1996, vol. 262, p. 732-745.*
Paul, W.E. Fundamental Immunology, 3rd Edition, 1993, p. 292-295.*
Rudikoff, S., et al. Single amino acid substitution altering antigen-binding specificity. Proc. Natl. Acad. Sci. USA. 1982, vol. 79, p. 1979-1983.*
Vajdos, F.F., et al. Comprehensive functional maps of the antigen-binding site of an anti-ErbB2 antibody obtained with shotgun scanning mutagenesis. J. Mol. Biol., 2002, vol. 320, p. 415-428.*
Wu, H., et al. Humanization of a murine monoclonal antibody by simultaneous optimization of framework and CDR residues. J. Mol. Biol., 1999, vol. 294, p. 151-162.*
International Search Report and Written Opinion of PCT/CN2017/102057 dated Dec. 22, 2017 (16 pages).

(Continued)

*Primary Examiner* — Joanne Hama
*Assistant Examiner* — Bruce D. Hissong
(74) *Attorney, Agent, or Firm* — Sheppard Mullin Richter & Hampton LLP

(57) ABSTRACT

Provided are anti-GM-CSF antibodies or fragments thereof including humanized antibodies and fragments. Also provided are uses of the antibodies and fragments for therapeutic, diagnostic and prognostic purposes. Therapeutic uses of the antibodies and fragments, for example include the treatment of inflammatory and autoimmune diseases and disorders.

22 Claims, 15 Drawing Sheets

Specification includes a Sequence Listing.

(56) References Cited

OTHER PUBLICATIONS

Behrens et al., "First in Patient Study of Anti-GM-CSF Monoclonal Antibody (MOR103) in Active Rheumatoid Artritis: Results of a Phase 1b/2a Randomized, Double-Blind, Placebo-Controlled Trial", Arthritis & Rheumatism; Annual Scientific Meeting of the American-College-of-Rheumatology and Association-of-Rheumatology-He; Washington, DC, USA; Nov. 10-14, 2012, Wiley Interscience, US, vol. 64. No. 12, Dec. 1, 2012, pp. 4171-4172, XP002733081, ISSN: 0004-3591 [retrieved on Nov. 28, 2012].

Constantinescu et al., "Randomized phase 1b trial of MOR103, a human antibody to GM-CSF, in multiple sclerosis", Neurology—Neuroimmunology Neuroinflammation, vol. 2, No. 4, May 21, 2015, p. e117, XP055540931, DOI: 20. 1212/NXI 0000000000000117.

Extended European Search Report of EP Patent Application No. 17840546.0 dated Mar. 4, 2019 (16 pages).

Hamilton, "GM-CSF in inflammation and autoimmunity", Trends in Immuno, Elsevier Ltd. *Trends Journals, GB, vol. 23, No. 8, Aug. 1, 2002, pp. 403-408, XP004371500, ISSN: 1471-4906, DOI: 10.106/S1471-4906(02)02260-3.

Krinner et al., "A human monoclonal IgG1 potently neutralizing the rpo-inflammantory cytokine GM-CSF", Molecular Immunol, Pergamon, GB, vol. 44, No. 5, Feb. 1, 2007, pp. 916-925, XP005663412, ISSN: 0161-5890, DOI: 10. 1016/J. Molimm. 2006.03.020 (retrieved on May 11, 2006).

Puljic et al, "Lipopolysaccharide-induced lung inflammation is inhibited by neutralization of GM-CSF", European Journal of Pharmaco, Elsevier Science, NL., vol. 557, No. 2-3, Feb. 3, 2007, pp. 230-235, XP005872830, ISSN: 0014-29999, DOI: 10.106/J. Ejphar. 2006.11.023

Shiomi et al., "GM-CSF as a therapeutic target in autoimmune diseases", Inflammation and Regeneration, vol. 36, No. 8, Jul. 5, 2016, pp. 1-9, XP055338930, DOI: 10.1186/s41232016-0014-5.

\* cited by examiner

ANTI-GM-CSF ANTIBODIES AND USES THEREOF

CROSS REFERENCE TO RELATED APPLICATIONS

The present application is the U.S. national stage application of International Application PCT/CN2017/102057, filed Sep. 18, 2017, which claims priority to Chinese Patent Application No. 201610831525.9, filed Sep. 19, 2016, and Chinese Patent Application No. 201610832677.0, filed Sep. 19, 2016, the contents of which are incorporated herein by reference in their entireties in the present disclosure.

SEQUENCE LISTING

The instant application contains a Sequence Listing which has been submitted in ASCII format via EFS-Web and is hereby incorporated by reference in its entirety. Said ASCII copy, created on Jan. 12, 2018, is named GMCSF_SEQ_ST25.txt and is 34,773 bytes in size.

BACKGROUND

Granulocyte-macrophage colony-stimulating factor (GM-CSF or GM-CSF), also known as colony stimulating factor 2 (CSF2), is a monomeric glycoprotein secreted by macrophages, T cells, mast cells, NK cells, endothelial cells and fibroblasts that functions as a cytokine. The pharmaceutical analogs of naturally occurring GM-CSF are also referred to as sargramostim and molgramostim. Unlike granulocyte colony-stimulating factor, which specifically promotes neutrophil proliferation and maturation, GM-CSF affects more cell types, especially macrophages and eosinophils.

GM-CSF is a monomeric glycoprotein that functions as a cytokine. GM-CSF stimulates stem cells to produce granulocytes (neutrophils, eosinophils, and basophils) and monocytes. Monocytes exit the circulation and migrate into tissue, whereupon they mature into macrophages and dendritic cells. Thus, it is part of the immune/inflammatory cascade, by which activation of a small number of macrophages can rapidly lead to an increase in their numbers, a process crucial for fighting infection. GM-CSF also has some effects on mature cells of the immune system. These include, for example, inhibiting neutrophil migration and causing an alteration of the receptors expressed on the cells surface.

GM-CSF signals via signal transducer and activator of transcription, STAT5. In macrophages, it has also been shown to signal via STAT3. The cytokine activates macrophages to inhibit fungal survival. It induces deprivation in intracellular free zinc and increases production of reactive oxygen species that culminate in fungal zinc starvation and toxicity. Thus, GM-CSF facilitates development of the immune system and promotes defense against infections. GM-CSF also plays a role in embryonic development by functioning as an embryokine produced by reproductive tract.

GM-CSF is manufactured using recombinant DNA technology and is marketed as a protein therapeutic called molgramostim or, when the protein is expressed in yeast cells, sargramostim. It is used as a medication to stimulate the production of white blood cells and thus prevent neutropenia following chemotherapy. GM-CSF has also been evaluated in clinical trials for its potential as a vaccine adjuvant in HIV-infected patients.

Inhibition of GM-CSF, by contrast, can be useful for treating diseases such as inflammatory diseases and autoimmune disorders including rheumatoid arthritis (OA), multiple sclerosis (MS) and plaque psoriasis. Inhibition of GM-CSF can also be useful for treating cancer.

SUMMARY

The present disclosure provides anti-GM-CSF antibody having high binding affinity to human GM-CSF proteins and having potent activities inhibiting the binding of GM-CSF to its receptor. These anti-GM-CSF antibodies are useful for therapeutic purposes such as treating various types of inflammatory diseases, autoimmune disorders and cancers, and can also be used for diagnostic and prognostic purposes.

The present disclosure, in one embodiment, provides an isolated antibody or fragment thereof, wherein the antibody or fragment thereof has specificity to a human GM-CSF protein and comprises a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6. In some embodiments, the antibody or fragment thereof further comprises a heavy chain constant region, a light chain constant region, an Fc region, or the combination thereof. In some embodiments, the light chain constant region is a kappa or lambda chain constant region. In some embodiments, the antibody or fragment thereof is of an isotype of IgG, IgM, IgA, IgE or IgD. In some embodiments, the isotype is IgG1, IgG2, IgG3 or IgG4. In some embodiments, the antibody or fragment thereof is a chimeric antibody, a humanized antibody, or a fully human antibody.

In some embodiments, the antibody or fragment thereof is a humanized antibody. In some embodiments, the antibody or fragment thereof comprises a heavy chain variable region comprising one or more amino acid residues selected from the group consisting of: (a) Glu at position 1, (b) Arg at position 98, (c) Ser at position 72, (d) Ala at position 68, (e) Leu at position 70, Ile at position 48, (g) Asp at position 26, and (h) Leu at position 29, according to Kabat numbering, and combinations thereof.

In some embodiments, the heavy chain variable region comprises a fragment of DYTLT (SEQ ID NO: 42) or GYTFT (SEQ ID NO: 43) starting at position 26 according to Kabat numbering.

In some embodiments, the antibody or fragment thereof comprises a light chain variable region comprising one or more amino acid residues selected from the group consisting of: (a) Ala at position 46, (b) Asp at position 60, (c) Asp at position 70, (d) Ser at position 43, and (f) Phe at position 87, according to Kabat numbering, and combinations thereof.

In some embodiments, the antibody or fragment thereof of comprises a heavy chain variable region comprising an amino acid sequence selected from the group consisting of SEQ ID NO: 8-17, or a peptide having at least 90% sequence identity to an amino acid sequence selected from the group consisting of SEQ ID NO: 8-17. In some embodiments, the heavy chain variable region comprises the amino acid sequence of SEQ ID NO: 11, 14 or 17.

In some embodiments, the antibody or fragment thereof comprises a light chain variable region comprising an amino acid sequence selected from the group consisting of SEQ ID NO: 19-22, or a peptide having at least 90% sequence identity to an amino acid sequence selected from the group consisting of SEQ ID NO: 19-22. In some embodiments, the light chain variable region comprises the amino acid sequence of SEQ ID NO: 19 or 22.

In some embodiments, the heavy chain variable region comprises the amino acid sequence of SEQ ID NO: 14 and the light chain variable region comprises the amino acid sequence of SEQ ID NO: 22. In some embodiments, the antibody or fragment thereof is a bispecific antibody or single chain variable fragment.

The present disclosure, in one embodiment, provides an isolated antibody or fragment thereof, wherein the antibody or fragment thereof has specificity to a human GM-CSF protein and comprises a VH CDR1 of SEQ ID NO: 23, a VH CDR2 of SEQ ID NO: 24, a VH CDR3 of SEQ ID NO: 25, a VL CDR1 of SEQ ID NO: 26, a VL CDR2 of SEQ ID NO: 27, and a VL CDR3 of SEQ ID NO: 28. In some embodiments, the antibody or fragment thereof further comprises a heavy chain constant region, a light chain constant region, an Fc region, or the combination thereof. In some embodiments, the light chain constant region is a kappa or lambda chain constant region. In some embodiments, the antibody or fragment thereof is of an isotype of IgG, IgM, IgA, IgE or IgD. In some embodiments, the isotype is IgG1, IgG2, IgG3 or IgG4. In some embodiments, the antibody or fragment thereof is a chimeric antibody, a humanized antibody, or a fully human antibody.

In some embodiments, the antibody or fragment thereof is a humanized antibody. In some embodiments, the antibody or fragment thereof comprises a heavy chain variable region comprising one or more amino acid residues selected from the group consisting of E1, R84, Y27, I28, I48, T68, L70, or T30, according to Kabat numbering, and combinations thereof.

In some embodiments, the heavy chain variable region comprises a fragment of GYIFT (SEQ ID NO: 44), GYIFS (SEQ ID NO: 45), or GGTFS (SEQ ID NO: 46) starting at position 26 according to Kabat numbering.

In some embodiments, the antibody or fragment thereof comprises a light chain variable region comprising one or more amino acid residues selected from the group consisting of: V48, D57, Q70 or S43, according to Kabat numbering, and combinations thereof.

In some embodiments, the antibody or fragment thereof of comprises a heavy chain variable region comprising an amino acid sequence selected from the group consisting of SEQ ID NO: 29-35, or a peptide having at least 90% sequence identity to an amino acid sequence selected from the group consisting of SEQ ID NO: 29-35. In some embodiments, the heavy chain variable region comprises the amino acid sequence of SEQ ID NO: 34 or 35.

In some embodiments, the antibody or fragment thereof comprises a light chain variable region comprising an amino acid sequence selected from the group consisting of SEQ ID NO: 36-41, or a peptide having at least 90% sequence identity to an amino acid sequence selected from the group consisting of SEQ ID NO: 36-41. In some embodiments, the light chain variable region comprises the amino acid sequence of SEQ ID NO: 38 or 39.

In some embodiments, the heavy chain variable region comprises the amino acid sequence of SEQ ID NO: 34 and the light chain variable region comprises the amino acid sequence of SEQ ID NO: 38. In some embodiments, the heavy chain variable region comprises the amino acid sequence of SEQ ID NO: 35 and the light chain variable region comprises the amino acid sequence of SEQ ID NO: 39. In some embodiments, the antibody or fragment thereof is a bispecific antibody or single chain variable fragment.

In one embodiment, provided is a composition comprising the antibody or fragment thereof of the present disclosure and a pharmaceutically acceptable carrier. Also provided, in one embodiment, is an isolated cell comprising one or more polynucleotide encoding the antibody or fragment thereof of the present disclosure.

In one embodiment, the present disclosure provides a method of treating an inflammatory or autoimmune disease or condition in a patient in need thereof, comprising administering to the patient the antibody or fragment thereof, or a composition of the present disclosure. Also provided are uses of the antibody or fragment thereof, or a composition for the manufacture of a medicament for treating an inflammatory or autoimmune disease or condition.

In some embodiments, the inflammatory disease or condition is selected from the group consisting of Alzheimer's disease, Addison's disease, atherosclerosis, ankylosing spondylitis, arthritis, osteoarthritis (OA), rheumatoid arthritis (RA), psoriatic arthritis (PA), ankylosing spondylitis, asthma, atherosclerosis, chronic obstructive pulmonary disease (COPD), Crohn's disease, colitis, dermatitis, diverticulitis, fibromyalgia, hepatitis, irritable bowel syndrome (IBS), systemic lupus erythematous (SLE), nephritis, Parkinson's disease (PD), vasculitis, and ulcerative colitis.

Also provided, in one embodiment, is a method of reducing or relieving pain in a patient in need thereof, comprising administering to the patient the antibody or fragment thereof of the present disclosure.

In some embodiments, the autoimmune disease or condition is selected from the group consisting of alopecia areata, autoimmune hemolytic anemia, autoimmune hepatitis, dermatomyositis, diabetes (type 1), celiac disease, autoimmune juvenile idiopathic arthritis, glomerulonephritis, Graves' disease, Guillain-Barré syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, autoimmune thyroiditis, Hashimoto's thyroiditis, autoimmune uveitis, vitiligo, and granulomatosis with polyangiitis (Wegener's).

Also provided is a method of detecting expression of GM-CSF in a sample, comprising contacting the sample with the antibody or fragment thereof under conditions for the antibody or fragment thereof to bind to the GM-CSF, and detecting the binding which indicates expression of GM-CSF in the sample.

DETAILED DESCRIPTION

Definitions

Figure 1:
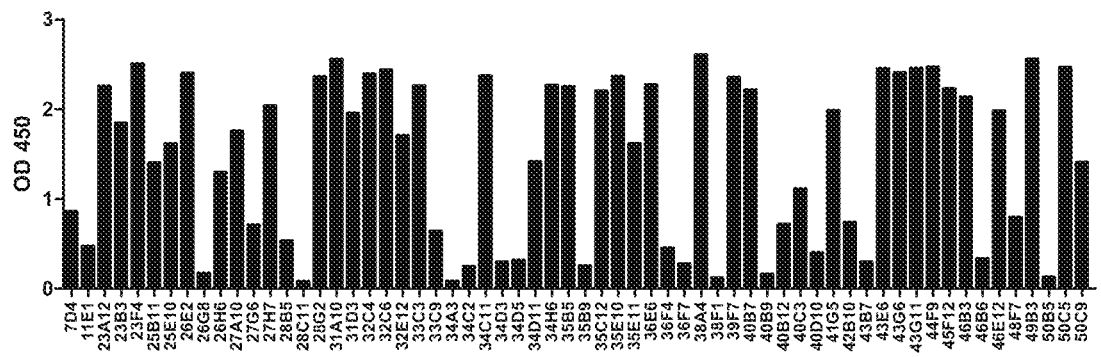
FIG. 1 shows results form confirmatory ELISA binding assays for selecting primary hybridoma clones for subcloning.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., saltbridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma$1-$\gamma$4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope D.

As used herein, the terms "treat" or "treatment" refer to both therapeutic treatment and prophylactic or preventative measures, wherein the object is to prevent or slow down (lessen) an undesired physiological change or disorder, such as the progression of an autoimmune disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-GM-CSF Antibodies

The present disclosure provides anti-GM-CSF antibodies with high affinity to the human GM-CSF protein. The tested antibodies exhibited potent binding and inhibitory activities and are useful for therapeutic and diagnostics uses. In addition to the original murine antibodies, the humanized ones also showed strong binding affinity to rhesus GM-CSF and human GM-CSF, which binding blocked the GM-CSF's binding to GM-CSF receptor alpha and blocked GM-CSF induced pSTAT5 signaling, and inhibited GM-CSF dependent TF-1 proliferation.

In accordance with one embodiment of the present disclosure, provided is an antibody that includes the heavy chain and light chain variable domains with the CDR regions as defined in SEQ ID NO: 1-6 or SEQ ID NO: 23-28, as shown below.

TABLE 1a

Sequences of the CDR regions of 23F4

| Name | Sequences | SEQ ID NO: |
|---|---|---|
| VH CDR1 | SHYLH | 1 |
| VH CDR2 | WIFPGDDKTKYNEKFKG | 2 |
| VH CDR3 | GTKYLNWNFDV | 3 |
| VL CDR1 | KANQNVGTTLA | 4 |
| VL CDR2 | SASYRYS | 5 |
| VL CDR3 | HQYTTYPLT | 6 |

TABLE 1b

Sequences of the CDR regions of 50C5

| Name | Sequences | SEQ ID NO: |
|---|---|---|
| VH CDR1 | PYSIH | 23 |
| VH CDR2 | YINPSTGYIEYNQHFKD | 24 |
| VH CDR3 | GGDYEGYFDY | 25 |
| VL CDR1 | RLNENIYSFLA | 26 |

TABLE 1b-continued

Sequences of the CDR regions of 50C5

| Name | Sequences | SEQ ID NO: |
|---|---|---|
| VL CDR2 | NAETLAE | 27 |
| VL CDR3 | QQHYGTPYT | 28 |

As demonstrated in the experimental examples, the antibodies that contained these CDR regions, whether mouse, humanized or chimeric, had potent GM-CSF binding and inhibitory activities. In some embodiments, an anti-GM-CSF antibody of the present disclosure includes the VH and VL CDR as listed in Table 1a-b, with one, two or three further modifications. Such modifications can be addition, deletion or substitution of amino acids.

In some embodiments, the modification is substitution at no more than one residues from each of the CDRs. In some embodiments, the modification is substitution at one, two or three residues. In one embodiment, the modification is substitution at one of the residues. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 2

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 |   |
| F | -4 | -5 | -5 | -3 | -4 | -3 | -6 | -5 | -4 | -5 | -2 | -5 | -4 | -1 | 0 | 1 | 2 | 9 |   |   |
| L | -6 | -4 | -3 | -3 | -2 | -2 | -4 | -3 | -3 | -2 | -2 | -3 | -3 | 2 | 4 | 2 | 6 |   |   |   |
| I | -2 | -3 | -2 | -1 | -1 | 0 | -2 | -2 | -2 | -2 | -2 | -2 | -2 | 4 | 2 | 5 |   |   |   |   |
| M | -5 | -3 | -2 | -2 | -1 | -1 | -3 | -2 | 0 | -1 | -2 | 0 | 0 | 2 | 6 |   |   |   |   |   |
| V | -2 | -1 | -1 | -1 | 0 | 0 | -2 | -2 | -2 | -2 | -2 | -2 | -2 | 4 |   |   |   |   |   |   |
| R | -4 | -3 | 0 | 0 | -2 | -1 | -1 | -1 | 0 | 1 | 2 | 3 | 6 |   |   |   |   |   |   |   |
| K | -5 | -2 | -1 | 0 | -1 | 0 | 0 | 0 | 1 | 1 | 0 | 5 |   |   |   |   |   |   |   |   |
| H | -3 | -2 | 0 | -1 | -1 | -1 | 1 | 1 | 2 | 3 | 6 |   |   |   |   |   |   |   |   |   |
| Q | -5 | -1 | 0 | -1 | 0 | -1 | 2 | 2 | 1 | 4 |   |   |   |   |   |   |   |   |   |   |
| N | -4 | 0 | -1 | 1 | 0 | 0 | 2 | 1 | 2 |   |   |   |   |   |   |   |   |   |   |   |
| E | -5 | 0 | -1 | 0 | 0 | 0 | 3 | 4 |   |   |   |   |   |   |   |   |   |   |   |   |
| D | -5 | 1 | -1 | 0 | 0 | 0 | 4 |   |   |   |   |   |   |   |   |   |   |   |   |   |
| T | -2 | 0 | 0 | 1 | 1 | 3 |   |   |   |   |   |   |   |   |   |   |   |   |   |   |
| A | -2 | 1 | 1 | 1 | 2 |   |   |   |   |   |   |   |   |   |   |   |   |   |   |   |
| S | 0 | 1 | 1 | 1 |   |   |   |   |   |   |   |   |   |   |   |   |   |   |   |   |
| P | -3 | -1 | 6 |   |   |   |   |   |   |   |   |   |   |   |   |   |   |   |   |   |
| G | -3 | 5 |   |   |   |   |   |   |   |   |   |   |   |   |   |   |   |   |   |   |
| C | 12 |   |   |   |   |   |   |   |   |   |   |   |   |   |   |   |   |   |   |   |

TABLE 3

Conservative Amino Acid Substitutions

| For Amino Acid | Substitution With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, an antibody or fragment thereof includes no more than one, no more than two, or no more than three of the above substitutions.

In some embodiments, the antibody or fragment thereof has specificity to a human GM-CSF protein and comprises a VH CDR1 of SEQ ID NO: 1, a VH CDR2 of SEQ ID NO: 2, a VH CDR3 of SEQ ID NO: 3, a VL CDR1 of SEQ ID NO: 4, a VL CDR2 of SEQ ID NO: 5, and a VL CDR3 of SEQ ID NO: 6. Non-limiting examples of VH are provided in SEQ ID NO: 7-17, out of which SEQ ID NO: 7 is the mouse VH, and SEQ ID NO: 8-17 are humanized ones. Further, these humanized VH include one or more back-mutations to the mouse version. Likewise, non-limiting examples of VL (VK) are provided in SEQ ID NO: 18-22. SEQ ID NO: 18 is a mouse sequence, and SEQ ID NO: 19-22 are humanized sequences, among which SEQ ID NO: 20-22 include one or more back-mutations, as shown in the examples.

The back-mutations are shown to be useful for retaining certain characteristics of the anti-GM-CSF antibodies. Accordingly, in some embodiments, the anti-GM-CSF antibodies of the present disclosure, in particular the human or humanized ones, include one or more of the back-mutations. In some embodiments, the VH back-mutation (i.e., included amino acid at the specified position) is one or more selected from (a) Glu at position 1 (E1), (b) Arg at position 98 (R98), (c) Ser at position 72 (S72), (d) Ala at position 68 (A68), (e) Leu at position 70 (L70), (f) Ile at position 48 (I48), (g) Asp at position 26 (D26), and (h) Leu at position 29 (L29), according to Kabat numbering, and combinations thereof.

In some embodiments, the humanized antibody includes at least VH back-mutation E1. In some embodiments, the humanized antibody includes at least VH back-mutations E1 and R98. In some embodiments, the humanized antibody includes at least VH back-mutations E1 and another as listed above. In some embodiments, the humanized antibody includes at least VH back-mutation group (E1, R98 and S72), (E1, R98, S72 and A68), (E1, R98, S72, A68, L70 and I48), (E1, R98, S72, A68, L70, I48, D26 and L29), (E1 and S72), (E1, S72 and L70), (E1, S72, L70, I48 and A68), (E1, S72, L70, I48, A68, D26 and L29).

In some embodiments, the heavy chain variable region comprises a fragment of DYTLT (SEQ ID NO: 42) or GYTFT (SEQ ID NO: 43) at the N-terminal end of the CDR1, i.e., starting at position 26 according to Kabat numbering. In one embodiment, the heavy chain variable region comprises DYTLT (SEQ ID NO: 42). In one embodiment, the heavy chain variable region comprises GYTFT (SEQ ID NO: 43).

In some embodiments, the humanized antibody includes one or more of the back-mutations. In some embodiments, the VL back-mutation is one or more selected from (a) Ala at position 46 (A46), (b) Asp at position 60 (D60), (c) Asp at position 70 (D70), (d) Ser at position 43 (S43), and (0 Phe at position 87 (F87), according to Kabat numbering, and combinations thereof.

In some embodiments, the humanized antibody includes at least two, three or four of VL back-mutations A46, D60, D70, S43, or F87. In some embodiments, the humanized antibody includes at least VL back-mutation A46. In some embodiments, the humanized antibody includes at least VL back-mutations A46 and D60 and another as listed above. In some embodiments, the humanized antibody includes at least VL back-mutation group (A46, D60 and D70) or (A46, D60, D70, S43 and F87).

In some embodiments, the humanized antibody includes at least VH back-mutations (E1, R98, S72, A68, L70 and I48) and no VL back-mutations. In some embodiments, the humanized antibody includes at least VH back-mutations (E1, S72, L70, I48, A68, D26 and L29) and no VL back-mutations. In some embodiments, the humanized antibody includes at least VH back-mutations (E1 and S72) and VL back-mutations (A46, D60, D70, S43 and F87).

In some embodiments, the anti-GM-CSF antibody of the present disclosure includes a VH of SEQ ID NO: 8-17, and a VL of SEQ ID NO: 19-22, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 10, therefore, can be a VH that has an overall 80%, 85%, 90%, 95%, 98% or 99% sequence identity to SEQ ID NO: 10 but retains the CDRs (SEQ ID NO: 1-3 or their variants), and optionally retains one or more, or all of the back-mutations.

In one embodiment, the VH has the amino acid sequence of SEQ ID NO: 11 and the VL has the amino acid sequence of SEQ ID NO: 19. In one embodiment, the VH has the amino acid sequence of SEQ ID NO: 17 and the VL has the amino acid sequence of SEQ ID NO: 19. In one embodiment, the VH has the amino acid sequence of SEQ ID NO: 11 and the VL has the amino acid sequence of SEQ ID NO: 22. Each of the recited sequences, it is noted, can also be substituted with their biological equivalents.

In some embodiments, the antibody or fragment thereof has specificity to a human GM-CSF protein and comprises a VH CDR1 of SEQ ID NO: 23, a VH CDR2 of SEQ ID NO: 24, a VH CDR3 of SEQ ID NO: 25, a VL CDR1 of SEQ ID NO: 26, a VL CDR2 of SEQ ID NO: 27, and a VL CDR3 of SEQ ID NO: 28. Non-limiting examples of VH are provided in SEQ ID NO: 29-35, out of which SEQ ID NO: 29 is the mouse VH, and SEQ ID NO: 30-35 are humanized ones. Further, these humanized VH include one or more back-mutations to the mouse version. Likewise, non-limiting examples of VL (VK) are provided in SEQ ID NO: 36-41. SEQ ID NO: 36 is a mouse sequence, and SEQ ID NO: 37-41 are humanized sequences, among which SEQ ID NO: 38-41 include one or more back-mutations, as shown in the examples.

The back-mutations are shown to be useful for retaining certain characteristics of the anti-GM-CSF antibodies. Accordingly, in some embodiments, the anti-GM-CSF antibodies of the present disclosure, in particular the human or humanized ones, include one or more of the back-mutations. In some embodiments, the VH back-mutation (i.e., included amino acid at the specified position) is one or more selected from E1, R84, Y27, I28, I48, T68, L70, or T30, according to Kabat numbering, and combinations thereof.

In some embodiments, the humanized antibody includes at least VH back-mutation E1. In some embodiments, the humanized antibody includes at least VH back-mutations E1 and R84. In some embodiments, the humanized antibody includes at least VH back-mutations E1 and another as listed above. In some embodiments, the humanized antibody includes at least VH back-mutation group (E1), (E1 and R84), (E1, R84, Y27 and I28), (E1, R84, Y27, I28 and I48), (E1, R84, Y27, I28, I48, T68 and L70), or (E1, R84, Y27, I28, I48, T68, L70 and T30).

In some embodiments, the heavy chain variable region comprises a fragment of GYIFT (SEQ ID NO: 44), GYIFS (SEQ ID NO: 45), or GGTFS (SEQ ID NO: 46) at the N-terminal end of the CDR1, i.e., starting at position 26 according to Kabat numbering. In one embodiment, the heavy chain variable region comprises GYIFT (SEQ ID NO: 44). In one embodiment, the heavy chain variable region comprises GYIFS (SEQ ID NO: 45). In one embodiment, the heavy chain variable region comprises GGTFS (SEQ ID NO: 46).

In some embodiments, the humanized antibody includes one or more of the back-mutations. In some embodiments, the VL back-mutation is one or more selected from V48, D57, Q70 or S43, according to Kabat numbering, and combinations thereof.

In some embodiments, the humanized antibody includes at least two, three or four of VL back-mutations V48, D57, Q70 or S43. In some embodiments, the humanized antibody includes at least VL back-mutation V48. In some embodiments, the humanized antibody includes at least VL back-mutations V48 and D57 and another as listed above. In some embodiments, the humanized antibody includes at least VL back-mutation group (V48), (V48 and D57), (V48, D57 and Q70) or (V48, D57, Q70 and S43).

In some embodiments, the humanized antibody includes at least VH back-mutations (E1, R84, Y27, I28, I48, T68 and L70) and VL back-mutation V48. In some embodiments, the humanized antibody includes at least VH back-mutations (E1, R84, Y27, I28, I48, T68, L70 and T30) and VL back-mutations (V48 and D57).

In some embodiments, the anti-GM-CSF antibody of the present disclosure includes a VH of SEQ ID NO: 30-35, and a VL of SEQ ID NO: 37-41, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 35, therefore, can be a VH that has an overall 80%, 85%, 90%, 95%, 98% or 99% sequence identity to SEQ ID NO: 35 but retains the CDRs (SEQ ID NO: 23-25 or their variants), and optionally retains one or more, or all of the back-mutations.

In one embodiment, the VH has the amino acid sequence of SEQ ID NO: 34 and the VL has the amino acid sequence of SEQ ID NO: 38. In one embodiment, the VH has the amino acid sequence of SEQ ID NO: 35 and the VL has the amino acid sequence of SEQ ID NO: 39. Each of the recited sequences, it is noted, can also be substituted with their biological equivalents.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

The antibodies and fragments of the present disclosure can be mono-specific or bispecific antibodies or fragments, in some embodiments. For a bispecific antibody, the other specificity can be to a different target epitope of GM-CSF or a different target protein which is useful for a particular use, e.g., therapeutic use. In one aspect, the target protein is s cytokine such as TNF-alpha, IL-6, IL-1, and IL-17. In another aspect, the target protein is a chemokine, such as CCL2, CXCL12, and CXCL13. In another aspect, the target protein is a cell surface protein, such as CD3, CSF-1R, CD20, and CD73.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated or connected by other means to another molecule to form a bi-functional molecule. The second molecule may be one of therapeutic agents, prodrugs, peptides, proteins, enzymes, viruses, lipids, biological response modifiers, pharmaceutical agents, or PEG. Some non-limiting examples are cytokines or other soluble factors, such as IL-10, IL-25, IL-27, IL-33, IL-35, and IL-36. Also provided, in some embodiments, are antibody-drug conjugates which include an antibody or fragment of the present disclosure and a small molecule drug.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 57:6851-6855 (1984); Morrison et al., Adv. Immunol. 44:65-92 (1988); Verhoeyen et al., Science 239:1534-1536 (1988); Padlan, Molec. Immun. 25:489-498 (1991); Padlan, Molec. Immun. 31:169-217 (1994), and U.S. Pat. Nos. 5,585,089, 5,693, 761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, Science 242:423-442 (1988); Huston et al., Proc. Natl. Acad. Sci. USA 55:5879-5883 (1988); and Ward et al., Nature 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in E. coli may also be used (Skerra et al., Science 242: 1038-1041 (1988)).

Examples of techniques which can be used to produce single-chain Fvs (scFvs) and antibodies include those described in U.S. Pat. Nos. 4,946,778 and 5,258,498; Huston et al., Methods in Enzymology 203:46-88 (1991); Shu et al., Proc. Natl. Sci. USA 90:1995-1999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA*:851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Treatment Methods and Uses

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies and fragments of the present disclosure, in some embodiments, can be used for manufacture of a medicament for treating an inflammatory or autoimmune disease or disorder, or cancer. It is also believed that the antibodies and fragments of the present disclosure are useful for treating the underlying mechanisms of pain or the pain itself.

Granulocyte-macrophage colony-stimulating factor (GM-CSF) was originally known by its ability to generate colonies of both granulocytes and macrophages from bone marrow precursors. It has also been shown to act on mature myeloid cells as pro-survival, activation, and differentiation factors. Recent studies suggest that GM-CSF also has many pro-inflammatory functions and plays critical roles in the development of autoimmune and inflammatory diseases.

GM-CSF promotes the survival and activation of macrophages, neutrophils, and eosinophils, as well as dendritic cell (DC) maturation. GM-CSF can polarize macrophages into M1-like inflammatory macrophages, which produce a variety of inflammatory cytokines such as TNF, IL-6, IL-12p70, IL-23, or IL-1β, and thus promote Th1-Th17 responses. On the other hand, the association of GM-CSF and Th2 immunity is also reported in allergic airway inflammation.

GM-CSF receptor consists of an α-subunit which binds GM-CSF with low affinity (GMRα) and a signal-transducing βc-subunit which is shared with the IL-3 and IL-5 receptors. The binary complex of GM-CSF and GMRα interacts with a free βc-subunit and forms the high-affinity hexamer complex. Dodecamer complexes formed by lateral aggregation of two hexamer complexes enable Jak2 associated with a βc-subunit to dimerize and transphosphorylate, but the hexamer complexes do not. This structure leads to dose-dependent responses of GM-CSF receptor activation. Low concentration of GM-CSF, as in normal condition, causes βc Ser585 phosphorylation and activates 14-3-3/PI-3 kinase pathway which only leads to cell survival. Higher concentration of GM-CSF, as in inflammatory condition, turns off βc Ser585 phosphorylation and mediated βc Tyr577 phosphorylation and activation of Jak2/STAT5 pathway, Ras/mitogen-activated protein kinase pathway, and PI-3 kinase pathway, resulting in promotion of cell survival, proliferation, and activation.

A wide variety of cells can produce GM-CSF. Major sources of GM-CSF are T and B cells, monocyte/macrophage endothelial cells, and fibroblasts. Neutrophils, eosinophils, epithelial cells, mesothelial cells, Paneth cells, chondrocytes, and tumor cells can also produce GM-CSF. The production of GM-CSF is stimulated by various factors, including TNF, IL-1, toll-like receptor agonists, and prostaglandin E2. Recently, the pathogenicity of GM-CSF-producing CD4 T cells in autoimmune and inflammatory diseases is clarified and gaining increasing attention.

Recent evidence revealed that GM-CSF played critical roles in the development of many autoimmune diseases. GM-CSF depletion or neutralization suppresses many autoimmune disease models, including experimental autoimmune encephalomyelitis (EAE), arthritis, arthritis-related interstitial lung disease, nephritis, or psoriasis. It is also suggested that inhibition of GM-CSF can be useful for treating cancer.

In some embodiments, the inflammatory disease or condition to be treated by the disclosed antibodies, fragments and compositions includes one or more of Alzheimer's disease, Addison's disease, atherosclerosis, ankylosing spondylitis, arthritis, osteoarthritis (OA), rheumatoid arthritis (RA), psoriatic arthritis (PA), ankylosing spondylitis, asthma, atherosclerosis, chronic obstructive pulmonary disease (COPD), Crohn's disease, colitis, dermatitis, diverticulitis, fibromyalgia, hepatitis, irritable bowel syndrome (IBS), systemic lupus erythematous (SLE), nephritis, Parkinson's disease (PD), vasculitis, and ulcerative colitis.

In some embodiments, the autoimmune disease or condition to be treated by the disclosed antibodies, fragments and compositions includes one or more of alopecia areata, autoimmune hemolytic anemia, autoimmune hepatitis, dermatomyositis, diabetes (type 1), celiac disease, autoimmune juvenile idiopathic arthritis, glomerulonephritis, Graves' disease, Guillain-Barré syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, autoimmune thyroiditis, Hashimoto's thyroiditis, autoimmune uveitis, vitiligo, and granulomatosis with polyangiitis (Wegener's).

Rheumatoid arthritis (RA) is a long-term autoimmune disorder that primarily affects joints. It typically results in warm, swollen, and painful joints. Pain and stiffness often worsen following rest. Most commonly, the wrist and hands are involved, with the same joints typically involved on both sides of the body. The disease may also affect other parts of the body. While the cause of rheumatoid arthritis is not clear, it is believed to involve a combination of genetic and environmental factors. The underlying mechanism involves the body's immune system attacking the joints. This results in inflammation and thickening of the joint capsule. The goals of treatment are to reduce pain, decrease inflammation, and improve a person's overall functioning. Pain medications, steroids, and NSAIDs are frequently used to help with symptoms. A group of medications called disease-modifying antirheumatic drugs (DMARDs), such as hydroxychloroquine and methotrexate, may be used to try to slow the progression of disease.

Osteoarthritis (OA) is a type of joint disease that results from breakdown of joint cartilage and underlying bone. The most common symptoms are joint pain and stiffness. Initially, symptoms may occur only following exercise, but over time may become constant. Other symptoms may include joint swelling, decreased range of motion, and when the back is affected weakness or numbness of the arms and legs. Causes include previous joint injury, abnormal joint or limb development, and inherited factors. Risk is greater in those who are overweight, have one leg of a different length, and have jobs that result in high levels of joint stress. Osteoarthritis is believed to be caused by mechanical stress on the joint and low grade inflammatory processes. Treatment includes exercise, efforts to decrease joint stress, support groups, and pain medications.

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. Specific symptoms can include double vision, blindness in one eye, muscle weakness, trouble with sensation, or trouble with coordination. While the cause is not clear, the underlying mechanism is thought to be either destruction by the immune system or failure of the myelin-producing cells. There is no known cure for multiple sclerosis. Treatments attempt to improve function after an attack and prevent new attacks.

Asthma is a common long-term inflammatory disease of the airways of the lungs. It is characterized by variable and recurring symptoms, reversible airflow obstruction, and bronchospasm. Symptoms include episodes of wheezing, coughing, chest tightness, and shortness of breath. Asthma is thought to be caused by a combination of genetic and environmental factors. Environmental factors include exposure to air pollution and allergens. Asthma is classified according to the frequency of symptoms, forced expiratory volume in one second (FEV1), and peak expiratory flow rate. It may also be classified as atopic or non-atopic, where atopy refers to a predisposition toward developing a type 1 hypersensitivity reaction. There is no cure for asthma. Symptoms can be prevented by avoiding triggers, such as allergens and irritants, and by the use of inhaled corticosteroids. Long-acting beta agonists (LABA) or antileukotriene agents may be used in addition to inhaled corticosteroids if asthma symptoms remain uncontrolled. Treatment of rapidly worsening symptoms is usually with an inhaled short-acting beta-2 agonist such as salbutamol and corticosteroids taken by mouth. In very severe cases, intravenous corticosteroids, magnesium sulfate, and hospitalization may be required.

Chronic obstructive pulmonary disease (COPD) is a type of obstructive lung disease characterized by long-term poor airflow. COPD can include two main conditions, emphysema and chronic bronchitis. In emphysema, the walls between many of the air sacs are damaged. As a result, the air sacs lose their shape and become floppy. This damage also can destroy the walls of the air sacs, leading to fewer and larger air sacs instead of many tiny ones. If this happens, the amount of gas exchange in the lungs is reduced. In chronic bronchitis, the lining of the airways stays constantly irritated and inflamed, and this causes the lining to swell. Lots of thick mucus forms in the airways, making it hard to breathe. There is no known cure for COPD, but the symptoms are treatable and its progression can be delayed.

Pain is a distressing feeling often caused by intense or damaging stimuli, such as stubbing a toe, burning a finger, putting alcohol on a cut, or bumping the "funny bone". Pain is a complex, subjective phenomenon, defining pain has been a challenge. Pain is also referred to as an unpleasant sensory and emotional experience associated with actual or potential tissue damage. Pain is sometimes regarded as a symptom of an underlying condition, such as inflammation.

In some embodiments, provided are methods for treating a cancer in a patient in need thereof. The method, in one embodiment, entails administering to the patient an effective amount of an antibody of the present disclosure.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antigen-binding polypeptide or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen-binding polypeptide or composition can be delivered in a controlled release system. In one embodiment, a pump may be used (see Sefton, 1987, CRC Crit. Ref. Biomed. Eng. 14:201; Buchwald et al., 1980, Surgery 88:507; Saudek et al., 1989, N. Engl. J Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

In a specific embodiment where the composition of the disclosure comprises a nucleic acid or polynucleotide encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances.

Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

Combination Compositions and Therapies

The anti-GM-CSF antibodies of the present disclosure can be used, in some embodiments, together with another therapeutic agent.

In some embodiment, the second therapeutic agent is an anti-inflammatory agent. Non-limiting examples include aspirin, ibuprofen, naproxen, celecoxib (Celebrex), piroxicam (Feldene), indomethacin (Indocin), meloxicam (Mobic Vivlodex), ketoprofen (Orudis, Ketoprofen ER, Oruvail, Actron), sulindac (Clinoril), diflunisal (Dolobid), nabumetone (Relafen), oxaprozin (Daypro), tolmetin (Tolmetin Sodium, Tolectin), salsalate (Disalcid), etodolac (Lodine), fenoprofen (Nalfon), flurbiprofen (Ansaid), ketorolac (Toradol), meclofenamate, and mefenamic acid (Ponstel).

In some embodiments, the second therapeutic agent is suitable for treating an autoimmune disease. Non-limiting examples include glucocorticoid, an anti-CD3 antibodies such as Muromonab-CD3, IL-2a inhibitors such as basiliximab (Simulect) and daclizumab (Zenapax), calcineurin inhibitors such as tacrolimus and ciclosporin, sirolimus, everolimus, interferons, opioids, TNF-binding proteins or antibodies, and mycophenolate.

In some embodiment, the second therapeutic agent is a cancer chemotherapeutic agent. Chemotherapeutic agents may be categorized by their mechanism of action into, for example, the following groups:

anti-metabolites/anti-cancer agents such as pyrimidine analogs floxuridine, capecitabine, and cytarabine;

purine analogs, folate antagonists, and related inhibitors;

antiproliferative/antimitotic agents including natural products such as vinca alkaloid (vinblastine, vincristine) and microtubule such as taxane (paclitaxel, docetaxel), vinblastin, nocodazole, epothilones, vinorelbine (NAVELBINE®), and epipodophyllotoxins (etoposide, teniposide);

DNA damaging agents such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin, mitoxantrone, nitrosourea, procarbazine, taxol, taxotere, teniposide, etoposide, and triethylenethiophosphoramide;

antibiotics such as dactinomycin, daunorubicin, doxorubicin, idarubicin, anthracyclines, mitoxantrone, bleomycins, plicamycin (mithramycin), and mitomycin;

enzymes such as L-asparaginase which systemically metabolizes L-asparagine and deprives cells which do not have the capacity to synthesize their own asparagine;

antiplatelet agents;

antiproliferative/antimitotic alkylating agents such as nitrogen mustards cyclophosphamide and analogs (melphalan, chlorambucil, hexamethylmelamine, and thiotepa), alkyl nitrosoureas (carmustine) and analogs, streptozocin, and triazenes (dacarbazine);

antiproliferative/antimitotic antimetabolites such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);
anticoagulants such as heparin, synthetic heparin salts, and other inhibitors of thrombin;
fibrinolytic agents such as tissue plasminogen activator, streptokinase, urokinase, aspirin, dipyridamole, ticlopidine, and clopidogrel;
antimigratory agents;
antisecretory agents (breveldin);
immunosuppressives tacrolimus, sirolimus, azathioprine, and mycophenolate;
compounds (TNP-470, genistein) and growth factor inhibitors (vascular endothelial growth factor inhibitors and fibroblast growth factor inhibitors);
angiotensin receptor blockers, nitric oxide donors;
anti-sense oligonucleotides;
antibodies such as trastuzumab and rituximab;
cell cycle inhibitors and differentiation inducers such as tretinoin;
inhibitors, topoisomerase inhibitors (doxorubicin, daunorubicin, dactinomycin, eniposide, epirubicin, etoposide, idarubicin, irinotecan, mitoxantrone, topotecan, and irinotecan), and corticosteroids (cortisone, dexamethasone, hydrocortisone, methylprednisolone, prednisone, and prednisolone);
growth factor signal transduction kinase inhibitors;
dysfunction inducers;
toxins such as Cholera toxin, ricin, *Pseudomonas* exotoxin, *Bordetella pertussis* adenylate cyclase toxin, diphtheria toxin, and caspase activators;
and chromatin.

Compositions

The present disclosure also provides pharmaceutical compositions. Such compositions comprise an effective amount of an antibody, and an acceptable carrier. In some embodiments, the composition further includes a second therapeutic agent.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1. Generation of Murine Antibodies

This example describes the process of preparing anti-human-GM-CSF mouse monoclonal antibodies using the hybridoma technology. Recombinant human GM-CSF protein was used as antigen. To generate mouse monoclonal antibodies to human GM-CSF, different strains of 6-8 week mice including BALB/c, C57/BL6 or SJL mice were firstly immunized with 20 µg recombinant human GM-CSF. On day 14, 28 and 42 post-first immunization, the immunized mice were re-immunized with 5 µg recombinant protein. To select mice producing antibodies that bond the GM-CSF protein, sera from immunized mice were tested by ELISA. Briefly, microtiter plates were coated with human GM-CSF protein at 1 µg/ml in PBS, 100 µl/well at room temperature (RT) overnight, then blocked with 100 µl/well of 5% BSA. Dilutions of plasma from immunized mice were added to each well and incubated for 1-2 hours at RT. The plates were washed with PBS/Tween and then incubate with anti-mouse IgG antibody conjugated with Horse Radish Peroxidase (HRP) for 1 hour at RT. After washing, the plates were developed with ABTS substrate and analyzed by spectrophotometer at OD 405 nm. Mice with sufficient titers of anti-GM-CSF IgG were boosted with 25 μg recombinant human GM-CSF protein at Day 60 post-immunization. The resulting mice were used for fusions.

Figure 2:
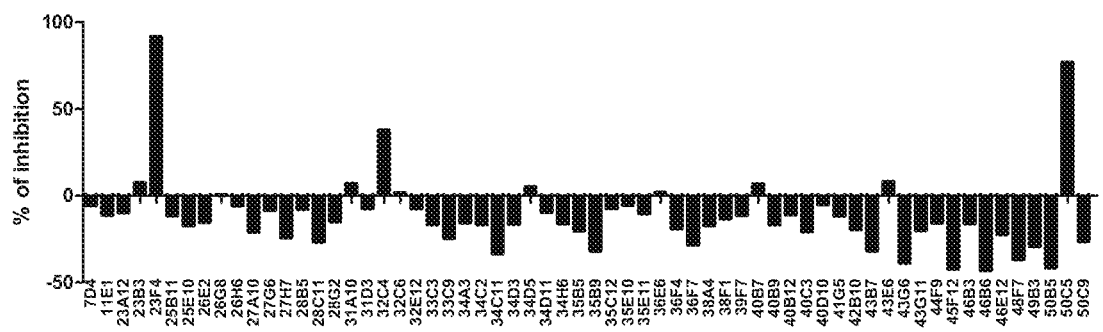
FIG. 2 shows results form confirmatory ELISA binding assays for selecting primary hybridoma clones for subcloning.

The hybridoma supernatants were tested for anti-GM-CSF IgGs by ELISA screening. The primary ELISA positive hybridoma clones were selected for subcloning using limited dilution method and further tested by confirmatory ELISA binding assay (FIG. 1) and TF-1 proliferation assay (FIG. 2). Prior to GM-CSF stimulation, TF-1 cells were washed with RPMI1640 basal medium and starved for over-night. At day 2, these starved cells were collected and then seeded at a concentration of $3 \times 10^5$ cells/ml in 50 μl per well of a flat bottom 96 well cell culture plate.

Human recombinant GM-CSF (Genscript) at a concentration of 0.2 ng/ml (4×) was 1:1 mixed 20% hybridoma culture supernatant (4×) and 50 μl of the mix was added to the TF-1 cells, so the final concentration for GM-CSF was 0.05 ng/ml and for hybridoma supernatant was 5%. Maximal cell proliferation (0% inhibition) was measured incubating TF-1 cells at a final concentration of GM-CSF of 0.05 ng/ml, without the addition of hybridoma supernatant. 100% inhibition of TF-1 proliferation was measured by omitting GM-CSF from the assay and keeping the cells in RPMI1640 complete medium only. TF-1 cells were then incubated for 72 hrs at 37° C. Cell viability was measured by CellTiter-Glo® Luminescent Cell Viability Assay according to the manufacturer's protocol.

Overall there were three hybridoma monoclones 23F4, 32C4 and 50O5 that showed significant inhibition of TF-1 proliferation while 23F4 and 50C5 were selected for further characterization.

Example 2. Binding of the Murine Antibodies to Human or Rhesus GM-CSF

This example tests the dose response of ELISA binding of mouse anti-GM-CSF mAb to recombinant human or rhesus GM-CSF protein (1 μg/ml@100 μl).

Recombinant human or rhesus GM-CSF protein (Genscript) was coated at 1 μg/ml in PBS onto microtiter plates for 2 h at room temperature (RT). After coating of antigen the wells were blocked with PBS/0.05% Tween (PBST) with 1% BSA for 1 h at RT. After washing of the wells with PBST, different concentrations of anti-GM-CSF antibodies were added to the well and incubated for 1 at RT. For detection of the binding antibodies, the HRP-conjugated secondary antibodies against mouse Fc (Jackson Immuno Research) were added, followed by the addition of fluorogenic substrates (Roche). Between all incubation steps, the wells of the plate were washed with PBST three times. Fluorescence was measured in a TECAN Spectrafluor plate reader.

Figure 3:
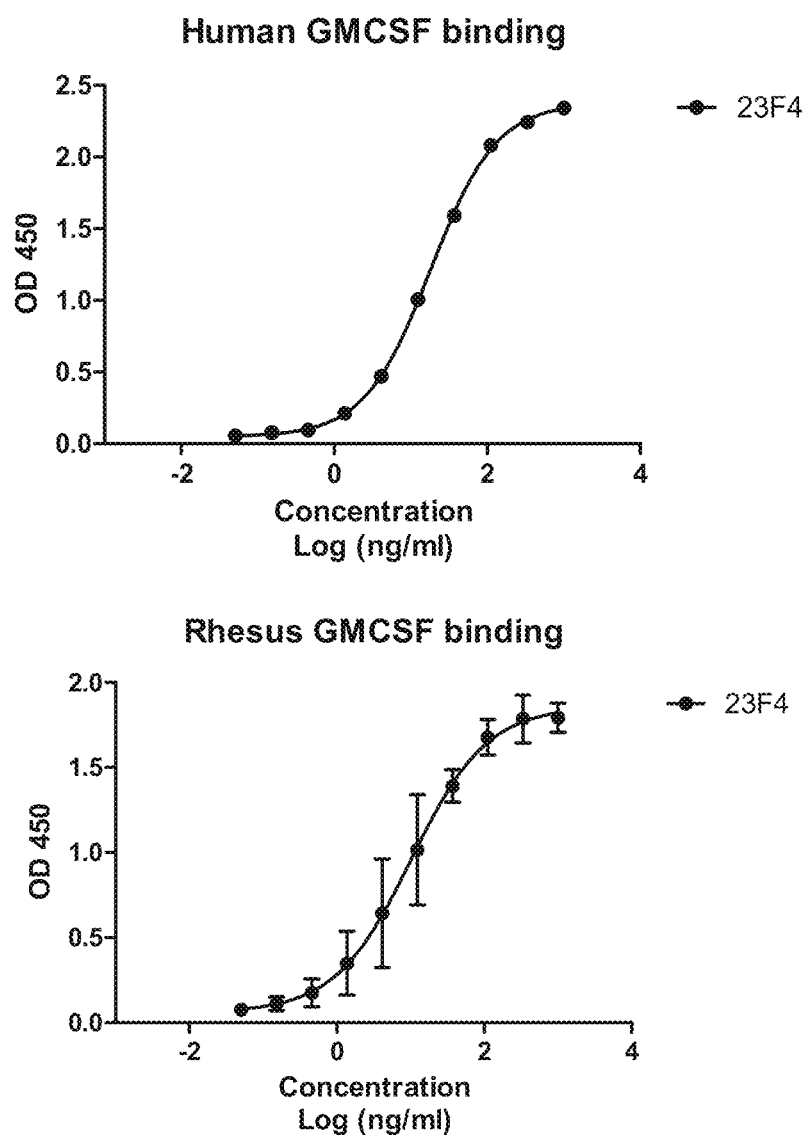
FIG. 3 shows dose-dependent binding of the test antibodies to human GM-CSF.
Figure 3:
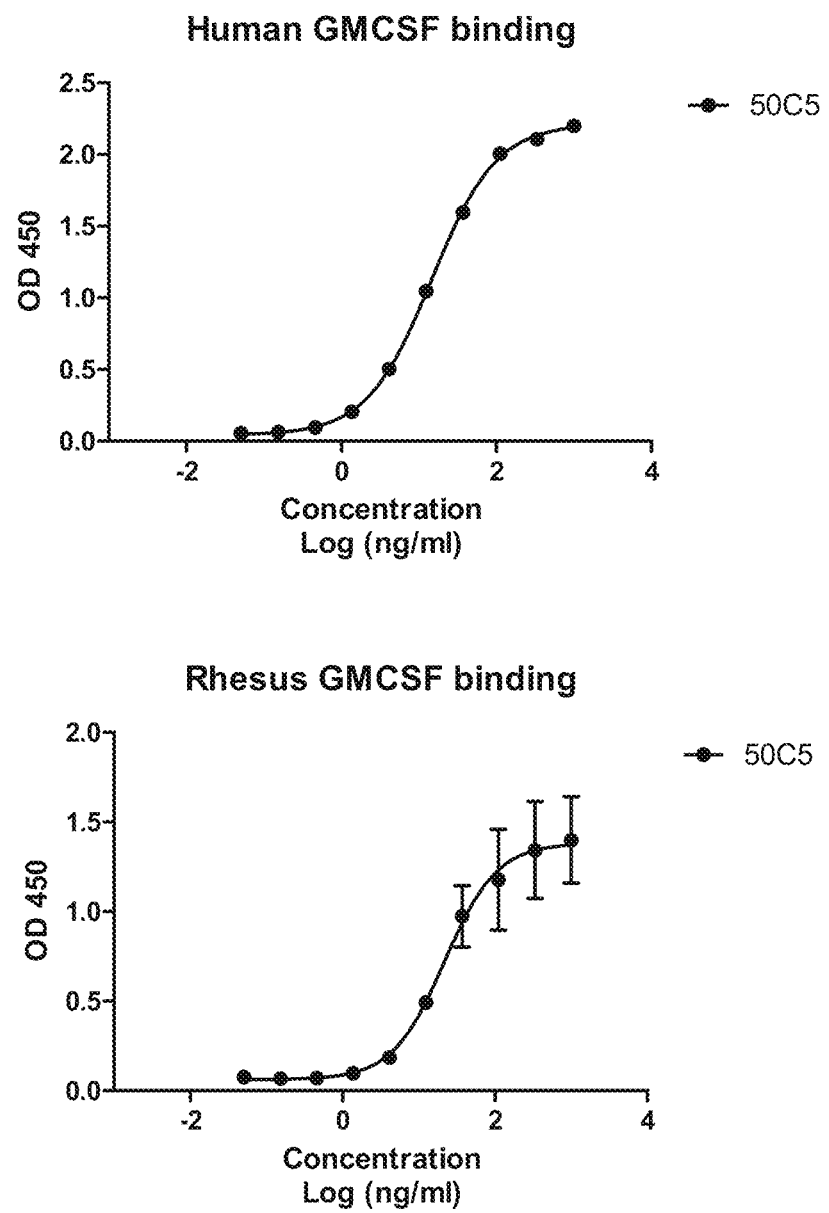

As shown in FIG. 3, both 23F4 and 50C5 antibodies showed dose-dependent binding to human GM-CSF with EC50s of 11.8 ng/ml and 14.6 ng/ml, respectively, and rhesus GM-CSF with EC50s of 10.2 ng/ml and 21.7 ng/ml, respectively.

Example 3. Binding Kinetics of the Murine Antibodies to Human GM-CSF

Figure 4:
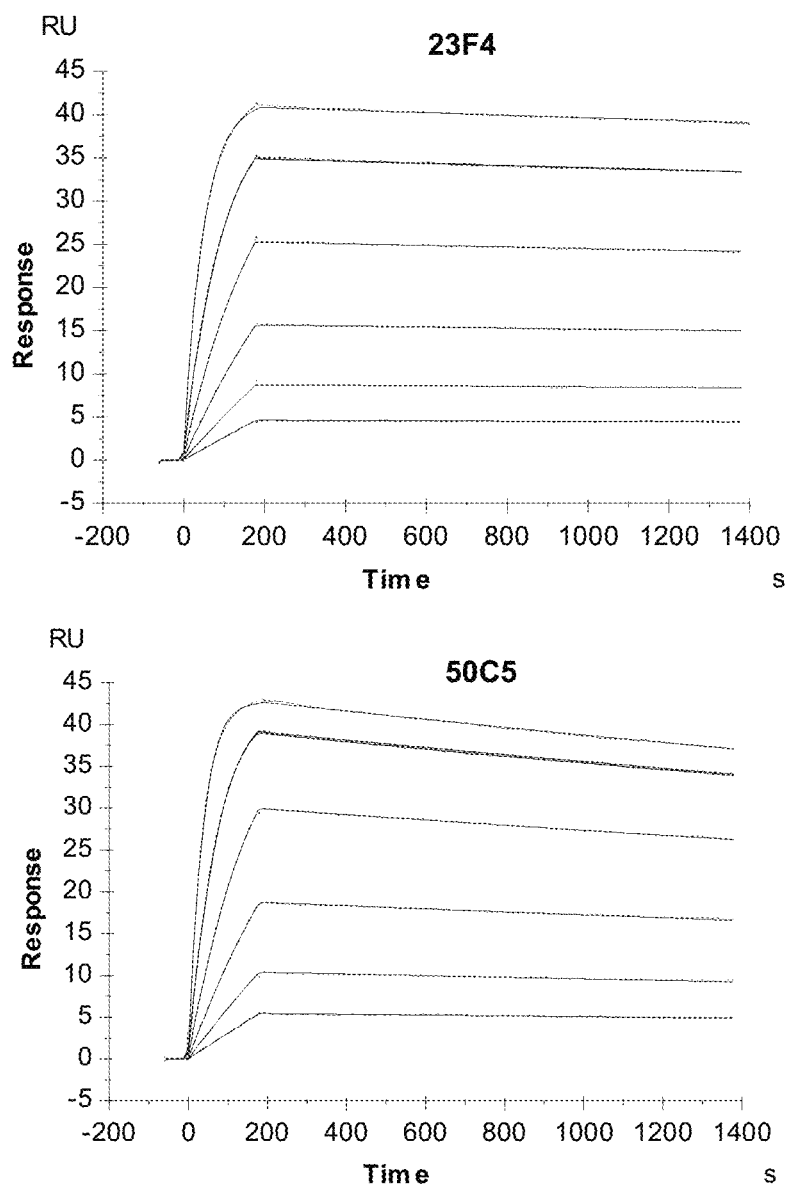
FIG. 4 plots the binding kinetics of antibodies with recombinant human GM-CSF.

FIG. 4 plots the binding kinetics of 23F4 and 50C5 with recombinant human GM-CSF. Recombinant human GM-CSF was set as an analyte with serial concentrations (100, 50, 25, 12.5, 6.25, 3.125 nM). The binding kinetics assay of antibody to antigen was performed using Biacore T200 system through a mouse antibody capture approach. The anti-mouse Fc IgG were immobilized on CM5 sensor chip according to the manufacturer's instruction. The test antibody was injected and captured by the immobilized anti-mouse Fc IgG. And then serial concentrations of the antigen were individually injected, and the binding profile was recorded for each concentration of antigen analyte, respectively. The assay system was regenerated by injection of 10 mM Glycine-HCL pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively.

The Biacore data were fitted using Biacore T200 evaluation software 1.0 according to 1:1 binding model to calculate the association (ka) and dissociation (kd) rate constants as well as the equilibrium constant (KD). In addition to FIG. 4, some summary data presented in the table below.

| Sample | ka (1/Ms) | kd (1/s) | KD (M) |
| --- | --- | --- | --- |
| 23F4 | 8.723E+05 | 3.635E−05 | 4.168E−11 |
| 50C5 | 2.718E+06 | 1.204E−04 | 4.431E−11 |

Example 4. Blocking of GM-CSF Binding to the GM-CSF Receptor Alpha by the Murine Antibodies In order to test the potency of the antibodies in the blockade of GM-CSF binding to the GM-CSF receptor alpha chain, recombinant human GM-CSF receptor alpha protein (CD116) was coated at 2 μg/ml in PBS onto microtiter plates for over-night at 4° C. After coating of antigen the wells were blocked with PBS/0.05% Tween (PBST) with 1% BSA for 1 h at RT. After washing of the wells with PBST, different concentrations of anti-GM-CSF antibodies were added to the well in the presence of biotinylated human GM-CSF protein (0.05 μg/ml) and incubated for 1 hr at RT.

Figure 5:
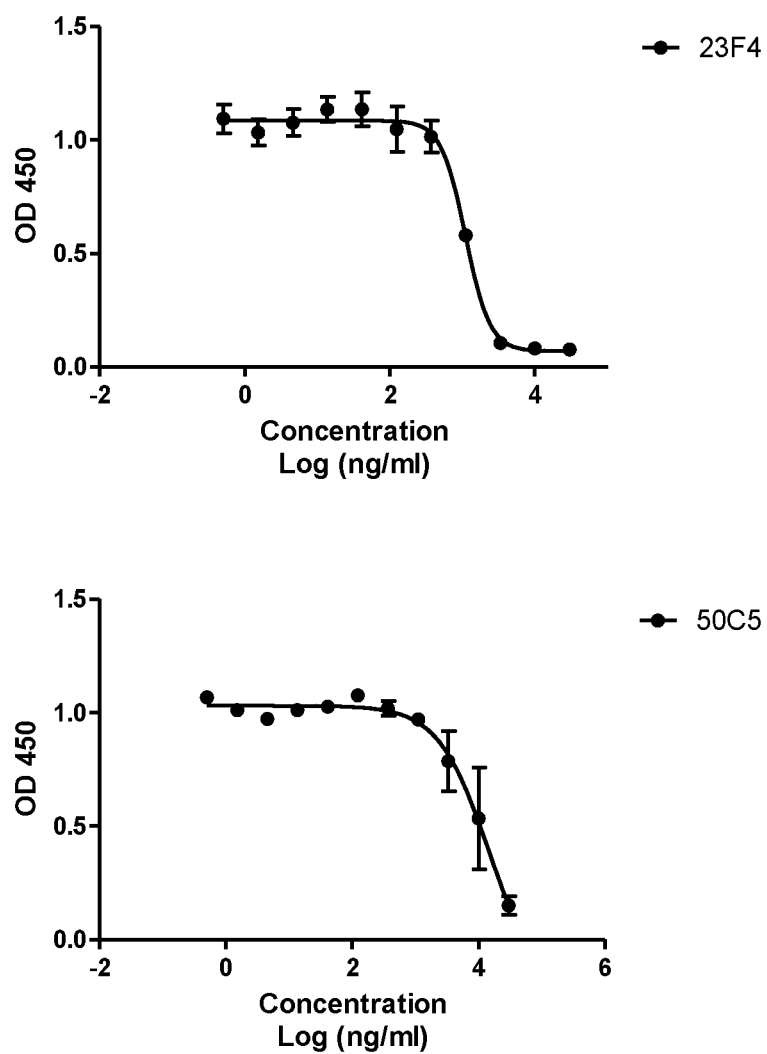
FIG. 5 shows dose-dependent inhibition of GM-CSF binding to the GM-CSF receptor alpha by the antibodies.

For detection of the binding of biotinylated GM-CSF to the coated receptor, the HRP-conjugated Streptavidin was added, followed by the addition of fluorogenic substrates (Roche). Between all incubation steps, the wells of the plate were washed with PBST three times. Fluorescence was measured in a TECAN Spectrafluor plate reader. As shown in FIG. 5, both antibodies showed dose-dependent inhibition of GM-CSF binding to the GM-CSF receptor alpha.

Figure 6:
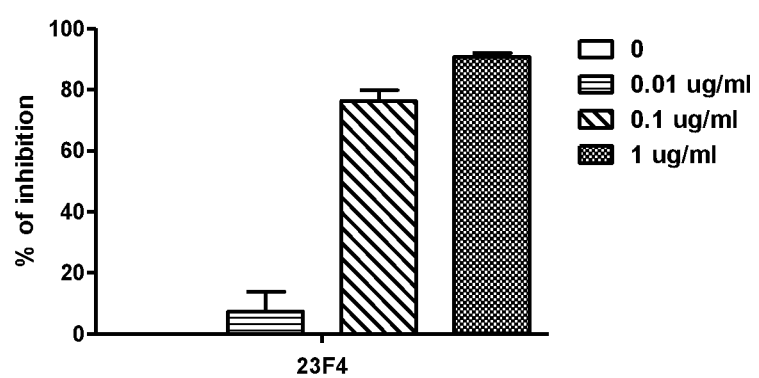
FIG. 6 shows that the antibodies significantly decreased the level of pSTAT5 activation induced by GM-CSF.
Figure 6:
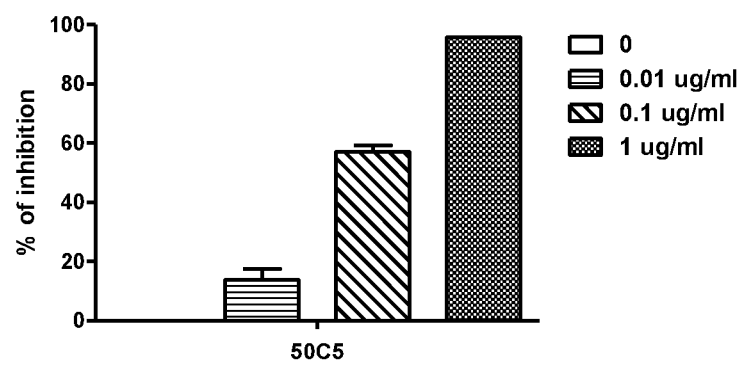

Example 5. Blocking of GM-CSF by the Murine Antibodies Induced pSTAT5 Signaling CD14+ monocytes were purified from peripheral human blood by using CD14 positive microbeads (Miltenyi Biotec). The purified monocytes were stimulated with human GM-CSF (0.2 ng/ml) for 30 minutes at 37° C. in the presence of different concentrations of 23F4 antibody. After incubation, the cells were collected and washed with FACS buffer (1× PBS+2% FBS) and permealized by 2% PFA followed by cell fixation using ice cold methanol. Then the PE-conjugated anti-pSTAT5 antibody was added to the cells for another incubation of 30 minutes at 4° C. and analyzed by flow cytometry. % of inhibition was calculated by [1−(MFI test sample/MFI control)]×100%. Addition of the antibodies could significantly decrease the level of pSTAT5 activation induced by GM-CSF at a dose of 0.1 or 1 μg/ml (FIG. 6).

Figure 7:
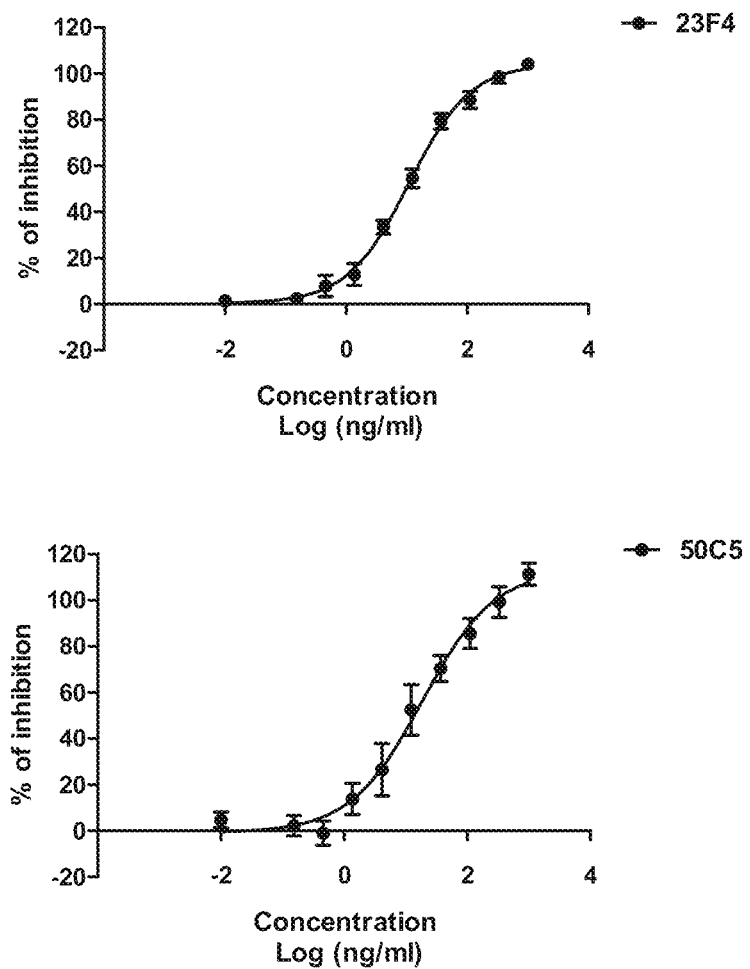
FIG. 7 shows the inhibition of GM-CSF dependent TF-1 proliferation by the antibodies.

Example 6. Inhibition of GM-CSF Dependent TF-1 Proliferation by the Murine Antibodies Prior to GM-CSF stimulation, TF-1 cells were washed with RPMI1640 basal medium and starved for over-night. At day 2, these starved cells were collected and then seeded at a concentration of 3×105 cells/ml in 50 μl per well of a flat bottom 96 well cell culture plate. Human recombinant GM-CSF (Genscript) at a concentration of 0.2 ng/ml (4×) was 1:1 mixed with murine anti-GM-CSF antibodies (0.01 ng/ml-1000 ng/ml diluted in complete medium) and 50 μl of the mix was added to the TF-1 cells. Maximal cell proliferation (0% inhibition) was measured incubating TF-1 cells at a final concentration of GM-CSF of 0.05 ng/ml, without the addition of antibody. 100% inhibition of TF-1 proliferation was measured by omitting GM-CSF from the assay and keeping the cells in RPMI1640 complete medium only. TF-1 cells were then incubated for 72 hrs at 37° C. Cell viability was measured by CellTiter-Glo® Luminescent Cell Viability Assay according to the manufacturer's protocol. The IC50 value for 23F4 and 50C5 in the inhibition of TF-1 proliferation were both about 10.9 ng/ml (FIG. 7).

Example 7. Humanization of the Murine Antibodies

The murine antibodies' variable region genes were employed to create humanized MAb. In the first step of this process, the amino acid sequences of the VH and VK of the antibodies were compared against the available database of human Ig gene sequences to find the overall best-matching human germline Ig gene sequences.

Humanized variable domain sequences were then designed where the CDR1, 2 and 3 of the antibody heavy and light chains were grafted onto framework sequences of the human Ig genes. A 3D model was then generated to determine if there were any framework positions where replacing the mouse amino acid to the human amino acid (back mutations) could affect binding and/or CDR conformation. The relevant sequences and back mutations are shown in the tables below.

CDR Sequences of 23F4 VH

```
CDR1
                                         (SEQ ID NO. 1)
SHYLH

CDR2
                                         (SEQ ID NO. 2)
WIFPGDDKTKYNEKFKG

CDR3
                                         (SEQ ID NO. 3)
GTKYLNWNFDV
```

CDR Sequences of 23F4 VL

```
CDR1
                                         (SEQ ID NO. 4)
KANQNVGTTLA

CDR2
                                         (SEQ ID NO. 5)
SASYRYS

CDR3
                                         (SEQ ID NO. 6)
HQYTTYPLT
```

Humanization Design for 23F4

| Construct | Mutation |
|---|---|
| VH Design I: VH1-f/JH6 | |
| 23F4 VH | Chimera |
| 23F4 VH.1 | CDR-grafted, Q1E, T98R |
| 23F4 VH.1a | Based on 23F4 VH.1, A72S |
| 23F4 VH.1b | Based on 23F4VH.1, A72S, V68A |
| 23F4 VH.1c | Based on 23F4VH.1, A72S, V68A, I70L, M48I |
| 23F4 VH.1d | Based on 23F4VH.1, A72S, V68A, I70L, M48I, G26D, F29L |
| VH Design II: VH1-f/JH6 | |
| 23F4 VH.2 | CDR-grafted, Q1E |
| 23F4 VH.2a | Based on 23F4 VH.2, R72S |
| 23F4 VH.2b | Based on 23F4 VH.2, R72S, M70L |
| 23F4 VH.2c | Based on 23F4 VH.2, R72S, M70L, M48I, V68A |
| 23F4 VH.2d | Based on 23F4 VH.2, R72S, M70L, M48I, V68A, G26D, F29L |
| VK Design: L8/Jk4 | |
| 23F4Vk | Chimera |
| 23F4 Vk.1 | CDR-grafted |
| 23F4 Vk.1a | Based on 23F4 Vk.1, L46A |
| 23F4 Vk.1b | Based on 23F4 Vk.1, L46A, S60D, E70D |
| 23F4 Vk.1c | Based on 23F4 Vk.1, L46A, S60D, E70D, A43S, Y87F |

The amino acid and nucleotide sequences of some of the humanized antibody 23F4 are listed in the table below. Humanized antibody sequences (CDR residues are underlined and back mutations are in Indicated Boxes)

| | | |
|---|---|---|
| 23F4 VH | QVQLQQSGPELVKPGTSMKISCKTSDYTLTSHYLHWVKQRPGQGLEWIGW IFPGDDKTKYNEKFKGKATLTSDKTSNTAYMQLSSLTSEESAVYFCARGT KYLNWNFDVWGTGTTVTVSS | SEQ ID NO. 7 |
| 23F4 VH.1 | [E]VQLVQSGAEVKKPGATVKISCKVSGYTFTSHYLHWVQQAPGKGLEWMGW IFPGDDKTKYNEKFKGRVTITADTSTDTAYMELSSLRSEDTAVYYCA[R]GT KYLNWNFDVWGQGTTVTVSS | SEQ ID NO. 8 |

| | | |
|---|---|---|
| 23F4 VH.1a | EVQLVQSGAEVKKPGATVKISCKVSGYTFTSHYLHWVQQAPGKGLEWMGW IFPGDDKTKYNEKFKGRVTITSDTSTDTAYMELSSLRSEDTAVYYCARGT KYLNWNFDVWGQGTTVTVSS | SEQ ID NO. 9 |
| 23F4 VH.1b | EVQLVQSGAEVKKPGATVKISCKVSGYTFTSHYLHWVQQAPGKGLEWMGW IFPGDDKTKYNEKFKGRATLTSDTSTDTAYMELSSLRSEDTAVYYCARGT KYLNWNFDVWGQGTTVTVSS | SEQ ID NO. 10 |
| 23F4 VH.1c | EVQLVQSGAEVKKPGATVKISCKVSGYTFTSHYLHWVQQAPGKGLEWIGW IFPGDDKTKYNEKFKGRAILISDTSTDTAYMELSSLRSEDTAVYYCARGT KYLNWNFDVWGQGTTVTVSS | SEQ ID NO. 11 |
| 23F4 VH.1d | EVQLVQSGAEVKKPGATVKISCKVSDYTLTSHYLHWVQQAPGKGLEWIGW IFPGDDKTKYNEKFKGRAILISDTSTDTAYMELSSLRSEDTAVYYCARGT KYLNWNFDVWGQGTTVTVSS | SEQ ID NO. 12 |
| 23F4 VH.2 | EVQLVQSGAEVKKPGASVKVSCKASGYTFTSHYLHWVRQAPGQGLEWMGW IFPGDDKTKYNEKFKGRVTMTRDTSISTAYMELSRLSDDTAVYYCARGT KYLNWNFDVWGQGTTVTVSS | SEQ ID NO. 13 |
| 23F4 VH.2a | EVQLVQSGAEVKKPGASVKVSCKASGYTFTSHYLHWVRQAPGQGLEWMGW IFPGDDKTKYNEKFKGRVTMTSDTSISTAYMELSRLSDDTAVYYCARGT KYLNWNFDVWGQGTTVTVSS | SEQ ID NO. 14 |
| 23F4 VH.2b | EVQLVQSGAEVKKPGASVKVSCKASGYTFTSHYLHWVRQAPGQGLEWMGW IFPGDDKTKYNEKFKGRVTLISDTSISTAYMELSRLSDDTAVYYCARGT KYLNWNFDVWGQGTTVTVSS | SEQ ID NO. 15 |
| 23F4 VH.2c | EVQLVQSGAEVKKPGASVKVSCKASGYTFTSHYLHWVRQAPGQGLEWIGW IFPGDDKTKYNEKFKGRAILISDTSISTAYMELSRLSDDTAVYYCARGT KYLNWNFDVWGQGTTVTVSS | SEQ ID NO. 16 |
| 23F4 VH.2d | EVQLVQSGAEVKKPGASVKVSCKASDYTLTSHYLHWVRQAPGQGLEWIGW IFPGDDKTKYNEKFKGRAILISDTSISTAYMELSRLSDDTAVYYCARGT KYLNWNFDVWGQGTTVTVSS | SEQ ID NO. 17 |
| 23F4Vk | DIVLTQPQKFLSTSVGDRVSVTCKANQNVGTTLAWYQQKPGQSPKALIYS ASYRYSGVPDRFTGSGSGTDFTLTISNVQSEDLAEYFCHQYTTYPLTFGG GTKLEIK | SEQ ID NO. 18 |
| 23F4 Vk.1 | DIQLTQSPSFLSASVGDRVTITCKANQNVGTTLAWYQQKPGKAPKLLIYS ASYRYSGVPSRFSGSGSGTEFTLTISSLQPEDFATYYCHQYTTYPLTFGG GTKVEIK | SEQ ID NO. 19 |
| 23F4 Vk.1a | DIQLTQSPSFLSASVGDRVTITCKANQNVGTTLAWYQQKPGKAPKALIYS ASYRYSGVPSRFSGSGSGTEFTLTISSLQPEDFATYYCHQYTTYPLTFGG GTKVEIK | SEQ ID NO. 20 |
| 23F4 Vk.1b | DIQLTQSPSFLSASVGDRVTITCKANQNVGTTLAWYQQKPGKAPKALIYS ASYRYSGVPDRFSGSGSGTDFTLTISSLQPEDFATYYCHQYTTYPLTFGG GTKVEIK | SEQ ID NO. 21 |

```
23F4 Vk.1c  DIQLTQSPSFLSASVGDRVTITCKANQNVGTTLAWYQQKPGKSPKALIYS  SEQ ID NO. 22
            ASYRYSGVPDRFSGSGSGTDFTLTISSLQPEDFATYFCHQYTTYPLTFGG
            GTKVEIK
```

Combination of VH/VK for Humanization Antibody 23F4

| VH | Vk | | | |
|---|---|---|---|---|
| | 23F4 Vk.1 | 23F4 Vk.1a | 23F4 Vk.1b | 23F4 Vk.1c | 23F4 Vk |
| 23F4 VH.1 | Hu23F4-1 | Hu23F4-2 | Hu23F4-3 | Hu23F4-4 | |
| 23F4 VH.1a | Hu23F4-5 | Hu23F4-6 | Hu23F4-7 | Hu23F4-8 | |
| 23F4 VH.1b | Hu23F4-9 | Hu23F4-10 | Hu23F4-11 | Hu23F4-12 | |
| 23F4 VH.1c | Hu23F4-13 | Hu23F4-14 | Hu23F4-15 | Hu23F4-16 | |
| 23F4 VH.1d | Hu23F4-17 | Hu23F4-18 | Hu23F4-19 | | |
| 23F4 VH.2 | Hu23F4-20 | Hu23F4-21 | Hu23F4-22 | Hu23F4-23 | |
| 23F4 VH.2a | Hu23F4-24 | Hu23F4-25 | Hu23F4-26 | Hu23F4-27 | |
| 23F4 VH.2b | Hu23F4-28 | Hu23F4-29 | Hu23F4-30 | Hu23F4-31 | |
| 23F4 VH.2c | Hu23F4-32 | Hu23F4-33 | Hu23F4-34 | Hu23F4-35 | |
| 23F4 VH.2d | Hu23F4-36 | Hu23F4-37 | Hu23F4-38 | | |
| 23F4 VH | | | | | 23F4 chimera |

CDR Sequences of 5005 VH

```
CDR1
                        (SEQ ID NO. 23)
PYSIH

CDR2
                        (SEQ ID NO. 24)
YINPSTGYIEYNQHFKD

CDR3
                        (SEQ ID NO. 25)
GGDYEGYFDY
```

CDR Sequences of 5005 VL

```
CDR1
                        (SEQ ID NO. 26)
RLNENIYSFLA

CDR2
                        (SEQ ID NO. 27)
NAETLAE

CDR3
                        (SEQ ID NO. 28)
QQHYGTPYT
```

Humanization Design for 5005

| Construct | Mutation |
|---|---|
| | VH Design I: VH1-69/JH6 |
| 50C5 VH | Chimera |
| 50C5 VH.1 | CDR-grafted, Q1E |
| 50C5 VH.1a | Based on 50C5 VH.1, S84R |
| 50C5 VH.1b | Based on 50C5 VH.1, S84R, G27Y, T28I |
| 50C5 VH.1c | Based on 50C5 VH.1, S84R, G27Y, T28I, M48I |
| 50C5 VH.1d | Based on 50C5 VH.1, S84R, G27Y, T28I, M48I, V68T, I70L |
| 50C5 VH.1e | Based on 50C5 VH.1, S84R, G27Y, T28I, M48I, V68T, I70L, S30T |
| | VK Design: O12/Jk4 |
| 50C5Vk | Chimera |
| 50C5 Vk.1 | CDR-grafted |
| 50C5 Vk.1a | Based on 50C5 Vk.1, I48V |
| 50C5 Vk.1b | Based on 50C5 Vk.1, I48V, G57D |
| 50C5 Vk.1c | Based on 50C5 Vk.1, I48V, G57D, D70Q |
| 50C5 Vk.1d | Based on 50C5 Vk.1, I48V, G57D, D70Q, A43S |

Humanized Antibody Sequences (CDR Residues are Underlined and Back Mutations are in Indicated Boxes)

```
50C5 VH    QVQLQQSAAELVRPGASVKMSCKASGYIFTPYSIHWIKQRPGQGLEWIGY  SEQ ID NO. 29
           INPSTGYIEYNQHFKDRTTLTADKSSSTAYMQLRSLTSEDSAVYYCARGG
           DYEGYFDYWGQGTTLTVSS

50C5 VH.1  EVQLVQSGAEVKKPGSSVKVSCKASGGTFSPYSIHWVRQAPGQGLEWMGY  SEQ ID NO. 30
           INPSTGYIEYNQHFKDRVTITADKSTSTAYMELSSLRSEDTAVYYCARGG
           DYEGYFDYWGQGTTVTVSS
```

-continued

| | | |
|---|---|---|
| 50C5 VH.1a | EVQLVQSGAEVKKPGSSVKVSCKASGGTFSPYSIHWVRQAPGQGLEWMGY INPSTGYIEYNQHFKDRVTITADKSTSTAYMELRSLRSEDTAVYYCARGG DYEGYFDYWGQGTTVTVSS | SEQ ID NO. 31 |
| 50C5 VH.1b | EVQLVQSGAEVKKPGSSVKVSCKASGYIFSPYSIHWVRQAPGQGLEWMGY INPSTGYIEYNQHFKDRVTITADKSTSTAYMELRSLRSEDTAVYYCARGG DYEGYFDYWGQGTTVTVSS | SEQ ID NO. 32 |
| 50C5 VH.1c | EVQLVQSGAEVKKPGSSVKVSCKASGYIFSPYSIHWVRQAPGQGLEWIGY INPSTGYIEYNQHFKDRVTITADKSTSTAYMELRSLRSEDTAVYYCARGG DYEGYFDYWGQGTTVTVSS | SEQ ID NO. 33 |
| 50C5 VH.1d | EVQLVQSGAEVKKPGSSVKVSCKASGYIFSPYSIHWVRQAPGQGLEWIGY INPSTGYIEYNQHFKDRTITADKSTSTAYMELRSLRSEDTAVYYCARGG DYEGYFDYWGQGTTVTVSS | SEQ ID NO. 34 |
| 50C5 VH.1e | EVQLVQSGAEVKKPGSSVKVSCKASGYIFTPYSIHWVRQAPGQGLEWIGY INPSTGYIEYNQHFKDRTITADKSTSTAYMELRSLRSEDTAVYYCARGG DYEGYFDYWGQGTTVTVSS | SEQ ID NO. 35 |
| 50C5 Vk | DIQMTQSPDSLSASVGETVTITCRLNENIYSFLAWYQQRQGKSPQLLVYNA ETLAEDVPSRFSGSGSGTQFSLKISSLQTDDFGTYYCQQHYGTPYTFGGGT NLEIE | SEQ ID NO. 36 |
| 50C5 Vk.1 | DIQMTQSPSSLSASVGDRVTITCRLNENIYSFLAWYQQKPGKAPKLLIYNA ETLAEGVPSRFSGSGSGTDFTLTISSLQPEDFATYYCQQHYGTPYTFGGGT KVEIK | SEQ ID NO. 37 |
| 50C5 Vk.1a | DIQMTQSPSSLSASVGDRVTITCRLNENIYSFLAWYQQKPGKAPKLLVYNA ETLAEGVPSRFSGSGSGTDFTLTISSLQPEDFATYYCQQHYGTPYTFGGGT KVEIK | SEQ ID NO. 38 |
| 50C5 Vk.1b | DIQMTQSPSSLSASVGDRVTITCRLNENIYSFLAWYQQKPGKAPKLLVYNA ETLAEDVPSRFSGSGSGTDFTLTISSLQPEDFATYYCQQHYGTPYTFGGGT KVEIK | SEQ ID NO. 39 |
| 50C5 Vk.1c | DIQMTQSPSSLSASVGDRVTITCRLNENIYSFLAWYQQKPGKAPKLLVYNA ETLAEDVPSRFSGSGSGTQFTLTISSLQPEDFATYYCQQHYGTPYTFGGGT KVEIK | SEQ ID NO. 40 |
| 50C5 Vk.1d | DIQMTQSPSSLSASVGDRVTITCRLNENIYSFLAWYQQKPGKSPKLLVYNA ETLAEDVPSRFSGSGSGTQFTLTISSLQPEDFATYYCQQHYGTPYTFGGGT KVEIK | SEQ ID NO. 41 |

Combination of VH/VK for Humanization Antibody 5005

| | Vk | | | | | |
|---|---|---|---|---|---|---|
| VH | 50C5 Vk.1 | 50C5 Vk.1a | 50C5 Vk.1b | 50C5 Vk.1c | 50C5 Vk.1d | 50C5 Vk |
| 50C5 VH.1 | | | | | | |
| 50C5 VH.1a | Hu50C5-1 | Hu50C5-2 | Hu50C5-3 | Hu50C5-4 | Hu50C5-5 | |
| 50C5 VH.1b | Hu50C5-6 | Hu50C5-7 | Hu50C5-8 | Hu50C5-9 | Hu50C5-10 | |
| 50C5 VH.1c | Hu50C5-11 | Hu50C5-12 | Hu50C5-13 | Hu50C5-14 | Hu50C5-15 | |
| 50C5 VH.1d | Hu50C5-16 | Hu50C5-17 | Hu50C5-18 | Hu50C5-19 | Hu50C5-20 | |

-continued

| | Vk | | | | | |
|---|---|---|---|---|---|---|
| VH | 50C5 Vk.1 | 50C5 Vk.1a | 50C5 Vk.1b | 50C5 Vk.1c | 50C5 Vk.1d | 50C5 Vk |
| 50C5 VH.1e | Hu50C5-21 | Hu50C5-22 | Hu50C5-23 | Hu50C5-24 | | |
| 50C5 VH | | | | | | 50C5 chimera |

Example 8. Binding of Humanized Antibodies to Human GM-CSF

The humanized variants were tested for the binding to recombinant human GM-CSF as previously described. Recombinant human GM-CSF protein (Genscript) was coated at 1 ug/ml in PBS onto microtiter plates for 2 h at room temperature (RT). After coating of antigen the wells were blocked with PBS/0.05% Tween (PBST) with 1% BSA for 1 h at RT. After washing of the wells with PBST, different concentrations of anti-GM-CSF humanized antibodies were added to the well and incubated for 1 at RT.

Figure 8:
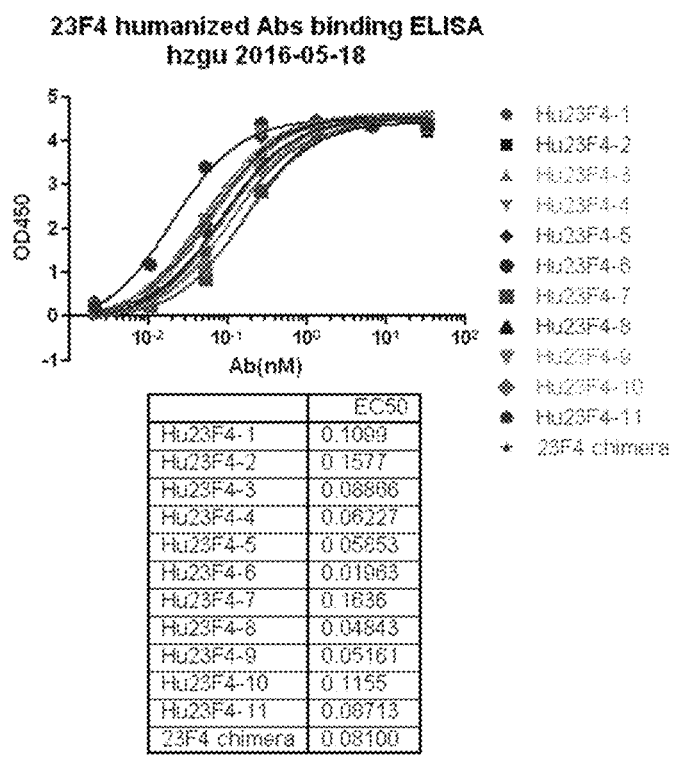
FIG. 8 shows that all the humanized antibodies demonstrated potent binding potency against human GM-CSF.
Figure 8:
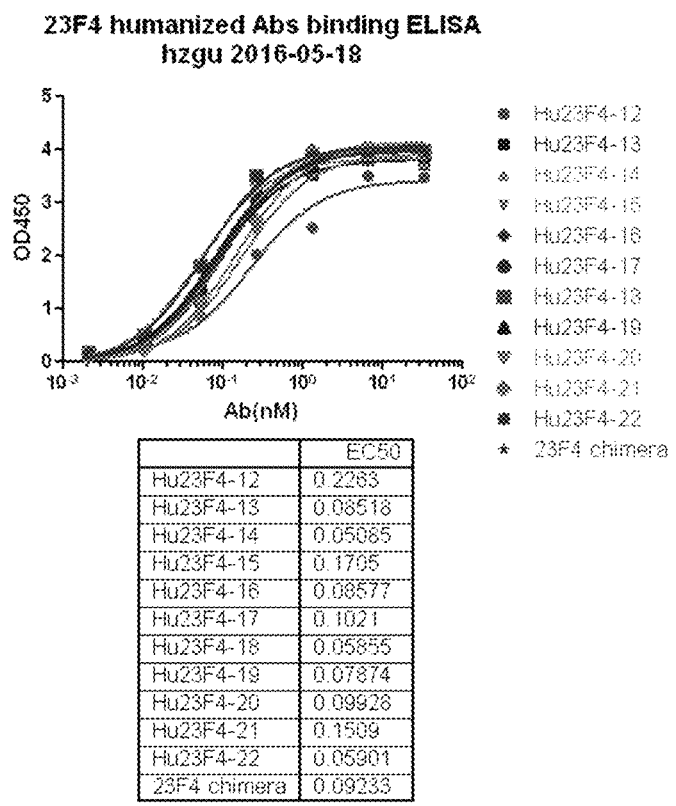
Figure 8:
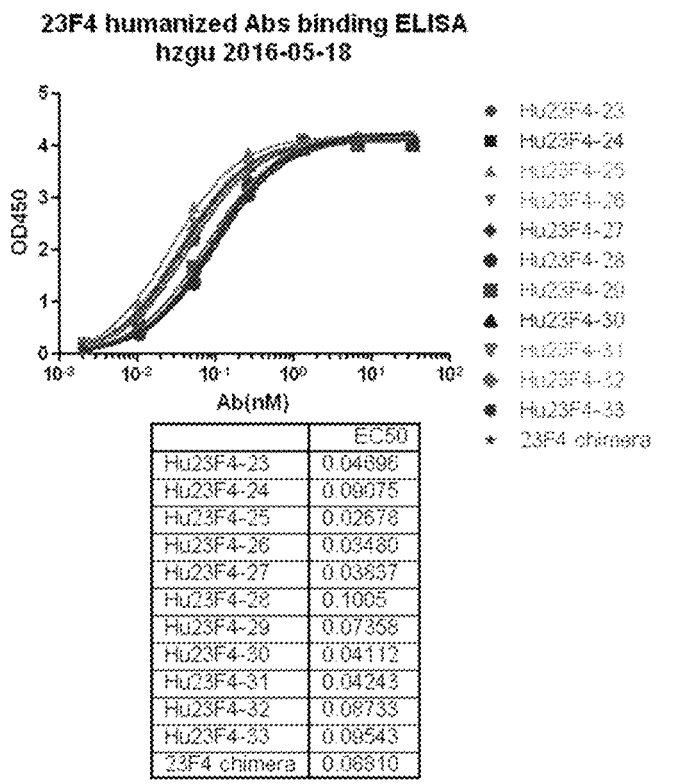
Figure 8:
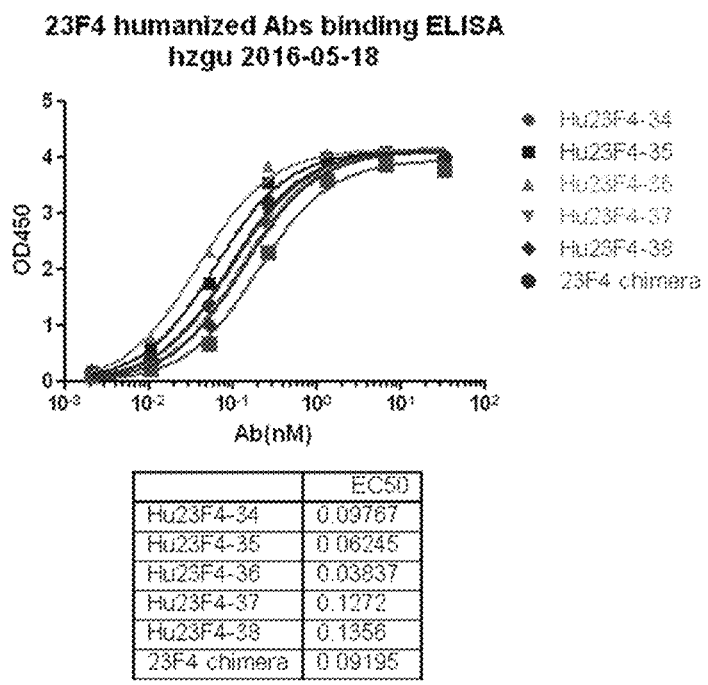
Figure 8:
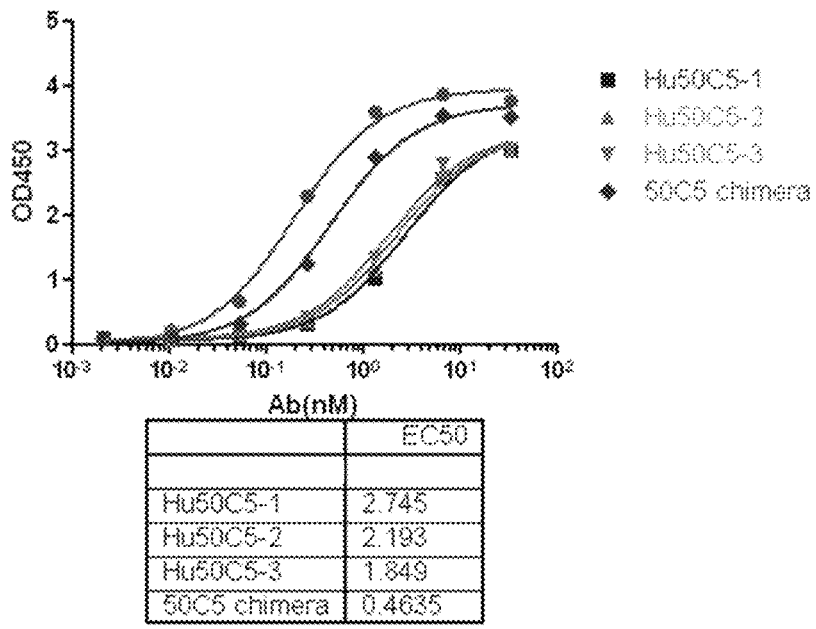
Figure 8:
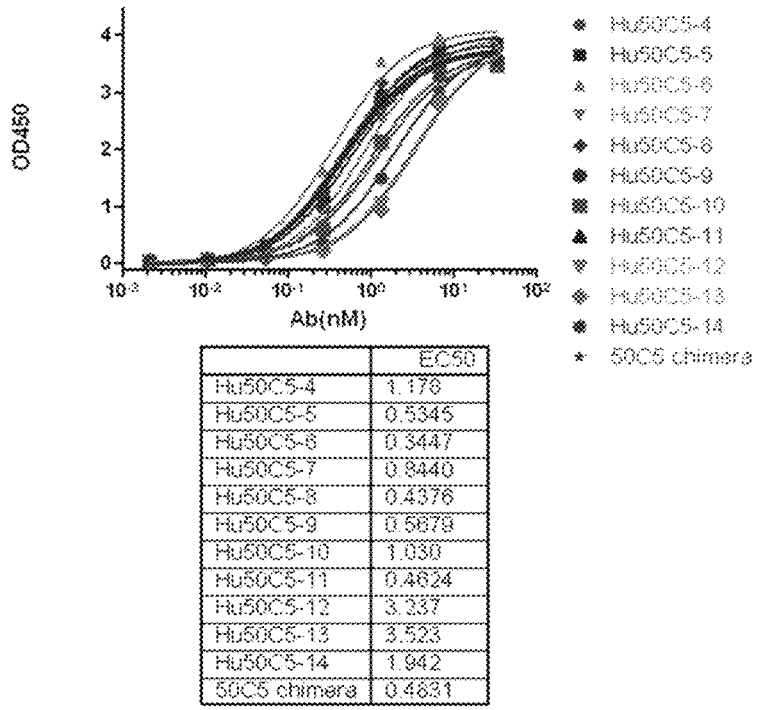
Figure 8:
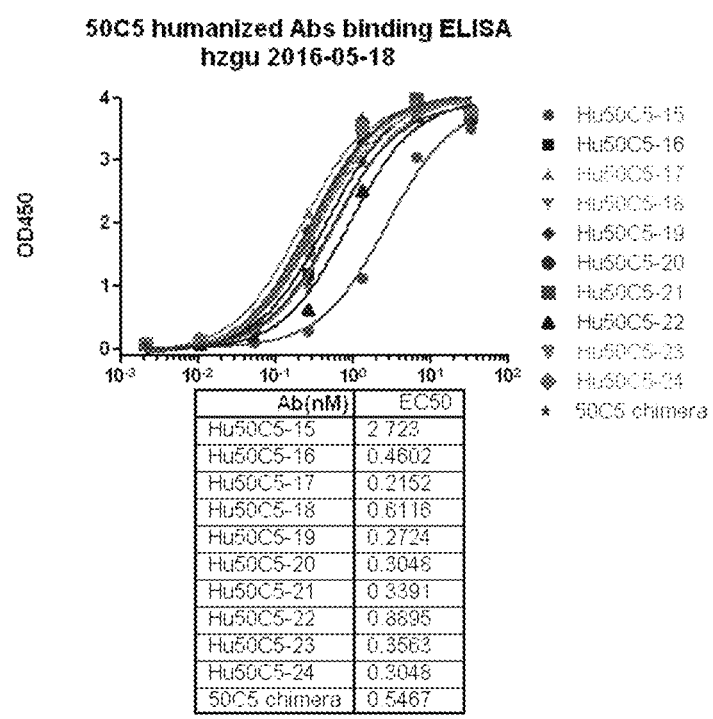

For detection of the binding antibodies, the HRP-conjugated secondary antibodies against mouse Fc (Jackson Immuno Research) were added, followed by the addition of fluorogenic substrates (Roche). Between all incubation steps, the wells of the plate were washed with PBST three times. Fluorescence was measured in a TECAN Spectrafluor plate reader. As shown in FIG. 8, all the humanized variants demonstrated a similar binding potency against human GM-CSF as compared with chimeric antibody.

Example 9. Binding Kinetics of Humanized Antibodies

The binding kinetics of humanized antibodies were measured by Biacore as previously described. Recombinant human GM-CSF was set as an analyte with serial concentrations (100, 50, 25, 12.5, 6.25, 3.125 nM). The binding kinetics assay of antibody to antigen was performed using Biacore T200 system through a human antibody capture approach. The anti-human Fc IgG were immobilized on CM5 sensor chip according to the manufacturer's instruction. The test antibody was injected and captured by the immobilized anti-human Fc IgG. And then serial concentrations of the antigen were individually injected, and the binding profile was recorded for each concentration of antigen analyte, respectively.

The assay system was regenerated by injection of 10 mM Glycine-HCL pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively. The Biacore data were fitted using Biacore T200 evaluation software 1.0 according to 1:1 binding model to calculate the association (ka) and dissociation (kd) rate constants as well as the equilibrium constant (KD). As shown in the tables below, from 23F4, Hu23F4-13, Hu23F4-27 and Hu23F4-36 demonstrated the strongest binding affinity as compared with chimeric antibody; from 5005, Hu50C5-8, Hu50C5-17, Hu50C5-18, Hu50C5-19, Hu50C5-21 and Hu50C5-23 demonstrated the strongest binding affinity as compared with chimeric antibody.

| Antigen | Antibody | ka (1/Ms) | kd (1/s) | KD (M) |
|---|---|---|---|---|
| GM-CSF | 3523-Hu23F4-5 | 1.188E+6 | 1.239E−4 | 1.043E−10 |
| | 3523-Hu23F4-6 | 8.76SE+S | 1.353E−4 | 1.544E−10 |
| | 3523-Hu23F4-13 | 1.279E+6 | 1.195E−4 | 9.349E−11 |
| | 3523-Hu23F4-20 | 8.007E+5 | 1.137E−4 | 1.420E−10 |
| | 3523-Hu23 F4-23 | 8.994E+5 | 1.164E−4 | 1.295E−10 |
| | 3523-Hu23 F4-25 | 6.354E+5 | 1.091E−4 | 1.718E−10 |
| | 3523-Hu23F4-27 | 9.232E+5 | 9.461E−5 | 1.025E−10 |
| | 3523-Hu23F4-29 | 6.673E+S | 1.013E−4 | 1.518E−10 |
| | 3523-Hu23F4-36 | 1.271E+6 | 1.026E−4 | 8.070E−11 |
| | 3523-Hu23F4-chimera | 1.229E+6 | 3.873E−5 | 3.150E−11 |
| | 35230Hu50C5-6 | 4.418E+6 | 1.375E−4 | 3.112E−11 |
| | 35230Hu50C5-8 | 4.911E+6 | 1.386E−4 | 2.822E−11 |
| | 35230Hu50C5-11 | 4.368E+6 | 1.363E−4 | 3.121E−11 |
| | 35230Hu50C5-17 | 4.466E+6 | 1.112E−4 | 2.491E−11 |
| | 35230Hu50C5-19 | 4.724E+6 | 1.089E−4 | 2.306E−11 |
| | 35230Hu50C5-19 | 4.622E+6 | 1.061E−4 | 2.295E−11 |
| | 35230Hu50C5-21 | 4.592E+6 | 1.082E−4 | 2.356E−11 |
| | 35230Hu50C5-23 | 4.535E+6 | 1.251E−4 | 2.760E−11 |
| | 35230Hu50C5-chimera | 4.433E+6 | 1.419E−4 | 3.202E−11 |

Example 10. Inhibition of TF-1 Proliferation by Humanized Antibodies

Figure 9:
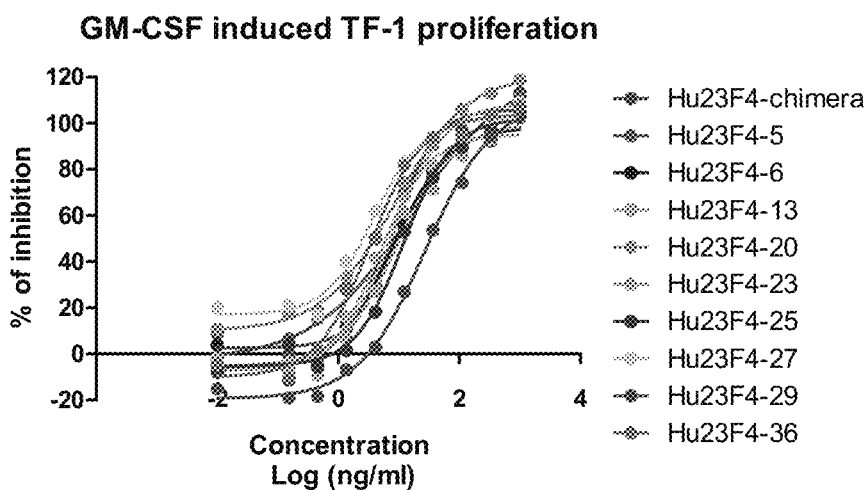
FIG. 9 shows that a few humanized antibodies exhibited strongest inhibition of TF-1 proliferation.
Figure 9:
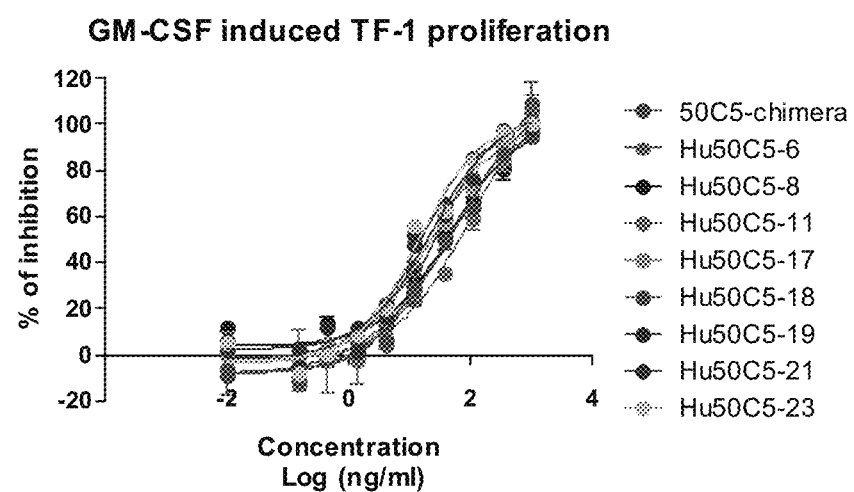

Prior to GM-CSF stimulation, TF-1 cells were washed with RPMI1640 basal medium and starved for over-night. At day 2, these starved cells were collected and then seeded at a concentration of 3×105 cells/ml in 50 ul per well of a flat bottom 96 well cell culture plate. Human recombinant GM-CSF (Genscript) at a concentration of 0.2 ng/ml (4×) was 1:1 mixed with humanized anti-GM-CSF antibodies (0.01 ng/ml-1000 ng/ml diluted in complete medium) and 50 ul of the mix was added to the TF-1 cells. Maximal cell proliferation (0% inhibition) was measured incubating TF-1 cells at a final concentration of GM-CSF of 0.05 ng/ml, without the addition of antibody. 100% inhibition of TF-1 proliferation was measured by omitting GM-CSF from the assay and keeping the cells in RPMI1640 complete medium only. TF-1 cells were then incubated for 72 hrs at 37° C. Cell viability was measured by CellTiter-Glo® Luminescent Cell Viability Assay according to the manufacturer's protocol. Among the humanized antibodies from 23F4 tested, Hu23F4-13, Hu23F4-27 and Hu23F4-36 showed strongest inhibition with an IC50 of 4.95 ng/ml, 3.95 ng/ml and 3.30 ng/ml, respectively (FIG. 9). Among the humanized antibodies from 5005 tested, Hu50C5-23 showed strongest inhibition with an IC50 of 14.31 ng/ml (FIG. 9).

| Antibody name | IC50 for TF-1 proliferation |
| --- | --- |
| Hu23F4-chimera | 8.55 ng/ml |
| Hu23F4-5 | 15.58 ng/ml |
| Hu23F4-6 | 7.87 ng/ml |
| Hu23F4-13 | 4.95 ng/ml |
| Hu23F4-20 | 8.77 ng/ml |
| Hu23F4-23 | 9.08 ng/ml |
| Hu23F4-25 | 12.22 ng/ml |
| Hu23F4-27 | 3.95 ng/ml |
| Hu23F4-29 | 27.44 ng/ml |
| Hu23F4-36 | 3.30 ng/ml |
| Hu50C5-chimera | 86.47 ng/ml |
| Hu50C5-6 | 23.93 ng/ml |
| Hu50C5-8 | 45.90 ng/ml |
| Hu50C5-11 | 111.1 ng/ml |
| Hu50C5-17 | 22.06 ng/ml |
| Hu50C5-18 | 41.27 ng/ml |
| Hu50C5-19 | 16.99 ng/ml |
| Hu50C5-21 | 21.64 ng/ml |
| Hu50C5-23 | 14.31 ng/ml |

Example 11. Blocking of pSTAT5 Signaling By Humanized Antibodies

Figure 10:
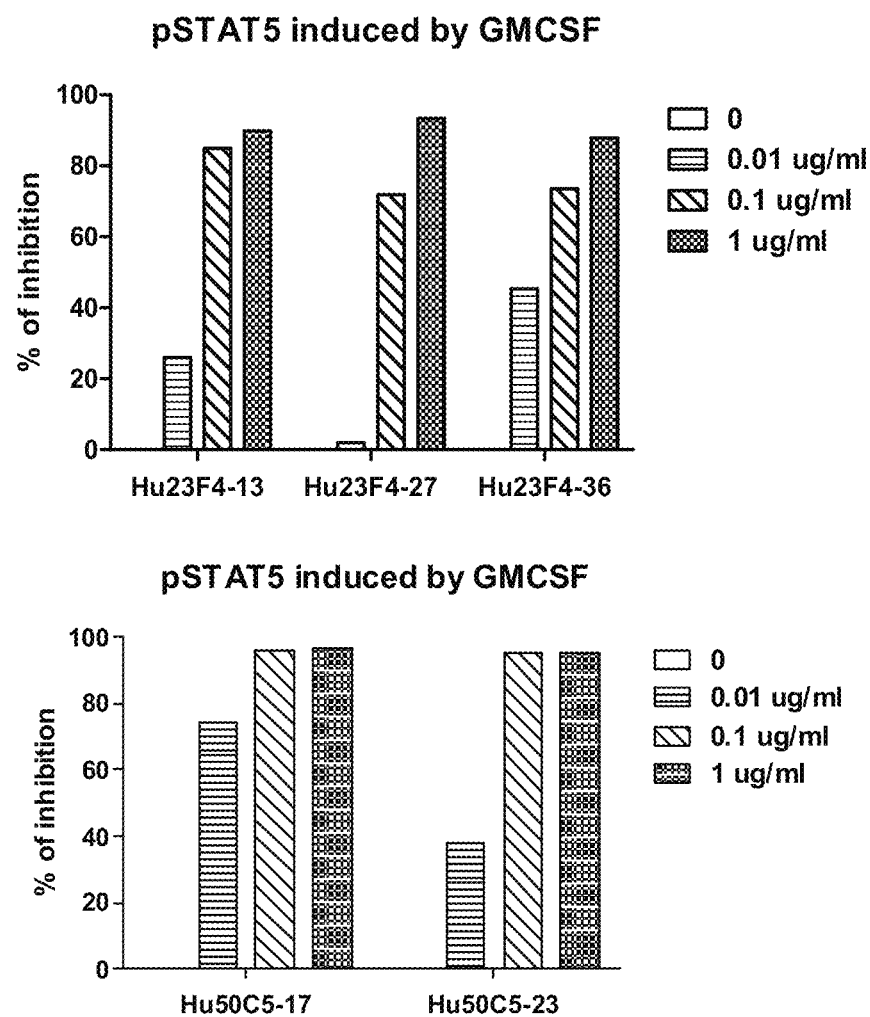
FIG. 10 shows that the tested antibodies effectively blocked pSTAT5 signaling.

CD14+ monocytes were purified from peripheral human blood by using CD14 positive microbeads (Miltenyi Biotec). The purified monocytes were stimulated with human GM-CSF (0.2 ng/ml) for 30 minutes at 37° C. in the presence of different concentrations of humanized antibodies. After incubation, the cells were collected and washed with FACS buffer (1×PBS+2% FBS) and permealized by 2% PFA followed by cell fixation using ice cold methanol. Then the PE-conjugated anti-pSTAT5 antibody was added to the cells for another incubation of 30 minutes at 4° C. and analyzed by flow cytometry. % of inhibition was calculated by [1−(MFI test sample/MFI control)]×100%. Addition of Hu23F4-13, Hu23F4-27, Hu23F4-36, Hu50C5-17 and Hu50C5-23 could significantly decrease the level of pSTAT5 activation induced by GM-CSF at a dose of 0.1 or 1 µg/ml (FIG. 10).

Example 12. Binding of Humanized Antibodies to Rhesus GM-CSF

Figure 11:
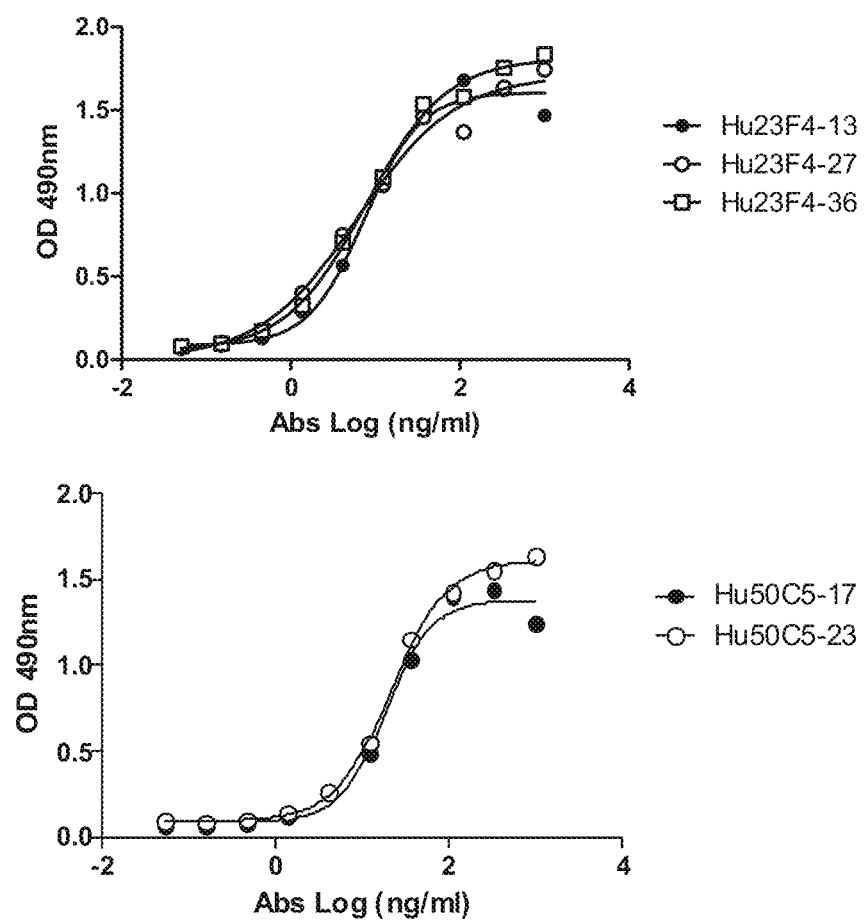
FIG. 11 shows dose-dependent binding of the antibodies to rhesus GM-CSF.

Recombinant rhesus GM-CSF protein (Genscript) was coated at 1 ug/ml in PBS onto microtiter plates for 2 h at room temperature (RT). After coating of antigen, the wells were blocked with PBS/0.05% Tween (PBST) with 1% BSA for 1 h at RT. After washing of the wells with PBST, different concentrations of humanized anti-GM-CSF antibodies were added to the well and incubated for 1 at RT. For detection of the binding antibodies, the HRP-conjugated secondary antibodies against mouse Fc (Jackson Immuno Research) were added, followed by the addition of fluorogenic substrates (Roche). Between all incubation steps, the wells of the plate were washed with PBST three times. Fluorescence was measured in a TECAN Spectrafluor plate reader. As shown in FIG. 11, Hu23F4-13, Hu23F4-27 and Hu23F4-36 showed a dose-dependent binding to rhesus GM-CSF with an EC50 of 7.44 ng/ml, 6.25 ng/ml and 7.75 ng/ml, respectively; Hu50C5-17 and Hu50C5-23 showed a dose-dependent binding to rhesus GM-CSF with an EC50 of 18.86 ng/ml and 21.63 ng/ml, respectively.

| Antibody name | EC50 for rhesus GM-CSF binding |
| --- | --- |
| Hu23F4-13 | 7.44 ng/ml |
| Hu23F4-27 | 6.25 ng/ml |
| Hu23F4-36 | 7.75 ng/ml |
| Hu50C5-17 | 18.86 ng/ml |
| Hu50C5-23 | 21.63 ng/ml |

Example 13. Pharmacokinetics of Hu23F4-27 in Cynomolgus Monkey

Figure 12:
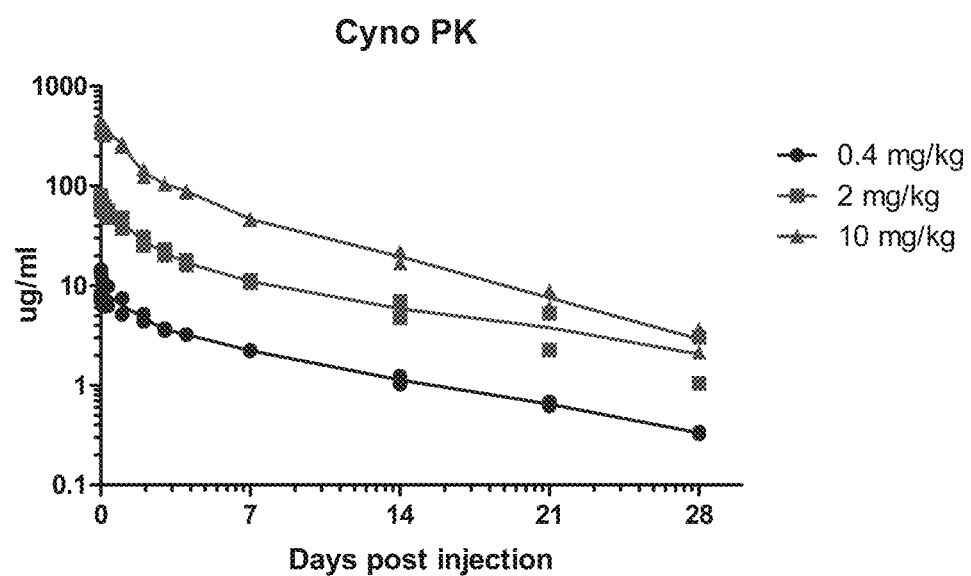
FIG. 12 plots the pharmacokinetics parameters of Hu23F4-27.

From the previous results of in vitro bio-activity assays, Hu23F4-27 was selected to determine the pharmacokinetics properties in naïve cynomolgus monkey. Hu23F4-27 antibody was administered by bolus intravenous injection to naïve cynomolgus monkey at different doses of 0.4 mg/kg, 2 mg/kg and 10 mg/kg, respectively. Plasma samples were collected at selected timepoints out to 28 days after dosing, and the concentration of the respective protein determined by ELISA. The pharmacokinetics parameters were then calculated using a non-compartmental approach with WinNonlin (Certara, Calif.) and shown in FIG. 12.

| Group (n = 2) | $T_{1/2}$ (h) | $C_{max}$ (µg/ml) | $AUC_{0-t}$ (Day*µg/ml) | $AUC_{inf}$ (day*µg/ml) | CL (ml/hr/kg) |
| --- | --- | --- | --- | --- | --- |
| 10 mg/kg | 121.4 ± 11.4 | 432.2 ± 31.7 | 1254.5 ± 38.3 | 1276.1 ± 48.6 | 0.327 ± 0.012 |
| 2 mg/kg | 220.7 ± 94.8 | 74.1 ± 8.3 | 280.3 ± 46.3 | 311.4 ± 76.6 | 0.276 ± 0.068 |
| 0.4 mg/kg | 178.2 ± 4.8 | 11.1 ± 4.6 | 49.4 ± 1.9 | 52.9 ± 1.7 | 0.315 ± 0.010 |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An isolated antibody or antigen-binding fragment thereof, wherein the antibody or fragment thereof has specificity to a human granulocyte macrophage colony-stimulating factor (GM-CSF) protein and comprises a heavy chain variable region (VH) complementarity determining region (CDR) 1 (CDR1) of SEQ ID NO: 1, a VH CDR2 of SEQ ID NO: 2, a VH CDR3 of SEQ ID NO: 3, a light chain variable region (VL) CDR1 of SEQ ID NO: 4, a VL CDR2 of SEQ ID NO: 5, and a VL CDR3 of SEQ ID NO: 6.

2. The antibody or antigen-binding fragment thereof of claim 1, further comprising a heavy chain constant region, a light chain constant region, an Fc region, or the combination thereof.

3. The antibody or antigen-binding fragment thereof of claim 2, wherein the light chain constant region is a kappa or lambda chain constant region.

4. The antibody or antigen-binding fragment thereof of claim 1, wherein the antibody or fragment thereof is of an isotype of IgG, IgM, IgA, IgE or IgD.

5. The antibody or antigen-binding fragment thereof of claim 1, wherein the antibody or fragment thereof is humanized.

6. The antibody or antigen-binding fragment thereof of claim 5, comprising a heavy chain variable region comprising one or more amino acid residues selected from the group consisting of:
  (a) Glu at position 1,
  (b) Arg at position 98,
  (c) Ser at position 72,
  (d) Ala at position 68,
  (e) Leu at position 70,
  (f) Ile at position 48,
  (g) Asp at position 26, and
  (h) Leu at position 29, according to Kabat numbering and with reference to SEQ ID NO:7, and combinations thereof.

7. The antibody or antigen-binding fragment thereof of claim 6, wherein the heavy chain variable region comprises at least (a) Glu at position 1.

8. The antibody or antigen-binding fragment thereof of claim 6, wherein the heavy chain variable region comprises a fragment comprising DYTLT (SEQ ID NO: 42) or GYTFT (SEQ ID NO: 43) starting at position 26 according to Kabat numbering.

9. The antibody or antigen-binding fragment thereof of claim 5, comprising a light chain variable region comprising one or more amino acid residues selected from the group consisting of:
  (a) Ala at position 46,
  (b) Asp at position 60,
  (c) Asp at position 70,
  (d) Ser at position 43, and
  (f) Phe at position 87, according to Kabat numbering and with reference to SEQ ID NO: 18, and combinations thereof.

10. The antibody or antigen-binding fragment thereof of claim 1, comprising a heavy chain variable region comprising an amino acid sequence selected from the group consisting of SEQ ID NO: 8-17.

11. The antibody or antigen-binding fragment thereof of claim 1, comprising a light chain variable region comprising an amino acid sequence selected from the group consisting of SEQ ID NO: 19-22.

12. The antibody or antigen-binding fragment thereof of claim 1, wherein the heavy chain variable region comprises the amino acid sequence of SEQ ID NO: 14 and the light chain variable region comprises the amino acid sequence of SEQ ID NO: 22.

13. A composition comprising the antibody or antigen-binding fragment thereof of claim 1 and a pharmaceutically acceptable carrier.

14. An isolated cell comprising one or more polynucleotides encoding the antibody or antigen-binding fragment thereof of claim 1.

15. A method of treating an inflammatory or autoimmune disease or condition in a patient in need thereof, comprising administering to the patient a therapeutically effective amount of the antibody or antigen-binding fragment thereof of claim 1.

16. The method of claim 15, wherein the inflammatory disease or condition is selected from the group consisting of Alzheimer's disease, Addison's disease, atherosclerosis, ankylosing spondylitis, arthritis, osteoarthritis (OA), rheumatoid arthritis (RA), psoriatic arthritis (PA), ankylosing spondylitis, asthma, atherosclerosis, chronic obstructive pulmonary disease (COPD), Crohn's disease, colitis, dermatitis, diverticulitis, fibromyalgia, hepatitis, irritable bowel syndrome (IBS), systemic lupus erythematous (SLE), nephritis, Parkinson's disease (PD), vasculitis, and ulcerative colitis.

17. The method of claim 15, wherein the autoimmune disease or condition is selected from the group consisting of alopecia areata, autoimmune hemolytic anemia, autoimmune hepatitis, dermatomyositis, diabetes (type 1), celiac disease, autoimmune juvenile idiopathic arthritis, glomerulonephritis, Graves' disease, Guillain-Barre syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjogren's syndrome, systemic lupus erythematosus, autoimmune thyroiditis, Hashimoto's thyroiditis, autoimmune uveitis, vitiligo, and granulomatosis with polyangiitis (Wegener's).

18. A method of treating a cancer in a patient in need thereof, comprising administering to the patient a therapeutically effective amount of the antibody or antigen-binding fragment thereof of claim 1.

19. The method of claim 18, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

20. The method of claim 18, further comprising administering to the patient an anti-cancer agent.

21. The method of claim 20, wherein the anti-cancer agent is selected from the group consisting of pyrimidine analog, purine analog, folate antagonist, DNA damaging agent, antimitotic alkylating agent, antimitotic antimetabolite, platinum coordination complex, and topoisomerase inhibitor.

22. A method of reducing or relieving pain in a patient in need thereof, comprising administering to the patient a therapeutically effective amount of the antibody or antigen-binding fragment thereof of claim 1.

\* \* \* \* \*

SEQUENCE LISTING

<160> NUMBER OF SEQ ID NOS: 46

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser His Tyr Leu His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Ile Phe Pro Gly Asp Asp Lys Thr Lys Tyr Asn Glu Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gly Thr Lys Tyr Leu Asn Trp Asn Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Lys Ala Asn Gln Asn Val Gly Thr Thr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ser Ala Ser Tyr Arg Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

```
<400> SEQUENCE: 6

His Gln Tyr Thr Thr Tyr Pro Leu Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Gln Val Gln Leu Gln Gln Ser Gly Pro Glu Leu Val Lys Pro Gly Thr
1               5                   10                  15

Ser Met Lys Ile Ser Cys Lys Thr Ser Asp Tyr Thr Leu Thr Ser His
            20                  25                  30

Tyr Leu His Trp Val Lys Gln Arg Pro Gly Gln Gly Leu Glu Trp Ile
        35                  40                  45

Gly Trp Ile Phe Pro Gly Asp Asp Lys Thr Lys Tyr Asn Glu Lys Phe
    50                  55                  60

Lys Gly Lys Ala Thr Leu Thr Ser Asp Lys Thr Ser Asn Thr Ala Tyr
65                  70                  75                  80

Met Gln Leu Ser Ser Leu Thr Ser Glu Glu Ser Ala Val Tyr Phe Cys
                85                  90                  95

Ala Arg Gly Thr Lys Tyr Leu Asn Trp Asn Phe Asp Val Trp Gly Thr
            100                 105                 110

Gly Thr Thr Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic

<400> SEQUENCE: 8

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser His
            20                  25                  30

Tyr Leu His Trp Val Gln Gln Ala Pro Gly Lys Gly Leu Glu Trp Met
        35                  40                  45

Gly Trp Ile Phe Pro Gly Asp Asp Lys Thr Lys Tyr Asn Glu Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 9
<211> LENGTH: 120
<212> TYPE: PRT
<213> ORGANISM: Artificial Sequence
```

```
<220> FEATURE:
<223> OTHER INFORMATION: Synthetic

<400> SEQUENCE: 9

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser His
            20                  25                  30

Tyr Leu His Trp Val Gln Gln Ala Pro Gly Lys Gly Leu Glu Trp Met
        35                  40                  45

Gly Trp Ile Phe Pro Gly Asp Asp Lys Thr Lys Tyr Asn Glu Lys Phe
    50                  55                  60

Lys Gly Arg Val Thr Ile Thr Ser Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser His
            20                  25                  30

Tyr Leu His Trp Val Gln Gln Ala Pro Gly Lys Gly Leu Glu Trp Met
        35                  40                  45

Gly Trp Ile Phe Pro Gly Asp Asp Lys Thr Lys Tyr Asn Glu Lys Phe
    50                  55                  60

Lys Gly Arg Ala Thr Leu Thr Ser Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser His
            20                  25                  30
```

Tyr Leu His Trp Val Gln Gln Ala Pro Gly Lys Gly Leu Glu Trp Ile
        35                  40                  45

Gly Trp Ile Phe Pro Gly Asp Asp Lys Thr Lys Tyr Asn Glu Lys Phe
50                      55                  60

Lys Gly Arg Ala Thr Leu Thr Ser Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic

<400> SEQUENCE: 12

Glu Val Gln Leu Val Gln Ser Gly Ala Glu Val Lys Lys Pro Gly Ala
1               5                   10                  15

Thr Val Lys Ile Ser Cys Lys Val Ser Asp Tyr Thr Leu Thr Ser His
            20                  25                  30

Tyr Leu His Trp Val Gln Gln Ala Pro Gly Lys Gly Leu Glu Trp Ile
        35                  40                  45

Gly Trp Ile Phe Pro Gly Asp Asp Lys Thr Lys Tyr Asn Glu Lys Phe
50                      55                  60

Lys Gly Arg Ala Thr Leu Thr Ser Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Leu His Trp Val Arg Gln Ala Pro Gly Gln Gly Leu Glu Trp Met
        35                  40                  45

Gly Trp Ile Phe Pro Gly Asp Asp Lys Thr Lys Tyr Asn Glu Lys Phe
50                      55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Leu His Trp Val Arg Gln Ala Pro Gly Gln Gly Leu Glu Trp Met
        35                  40                  45

Gly Trp Ile Phe Pro Gly Asp Asp Lys Thr Lys Tyr Asn Glu Lys Phe
    50                  55                  60

Lys Gly Arg Val Thr Met Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
            115                 120

<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Leu His Trp Val Arg Gln Ala Pro Gly Gln Gly Leu Glu Trp Met
        35                  40                  45

Gly Trp Ile Phe Pro Gly Asp Asp Lys Thr Lys Tyr Asn Glu Lys Phe
    50                  55                  60

Lys Gly Arg Val Thr Leu Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
            115                 120

<210> SEQ ID NO 16
<211> LENGTH: 120
<212> TYPE: PRT
<213> ORGANISM: Artificial Sequence -continued
<220> FEATURE:
<223> OTHER INFORMATION: Synthetic

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Leu His Trp Val Arg Gln Ala Pro Gly Gln Gly Leu Glu Trp Ile
        35                  40                  45

Gly Trp Ile Phe Pro Gly Asp Asp Lys Thr Lys Tyr Asn Glu Lys Phe
    50                  55                  60

Lys Gly Arg Ala Thr Leu Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Asp Tyr Thr Leu Thr Ser His
            20                  25                  30

Tyr Leu His Trp Val Arg Gln Ala Pro Gly Gln Gly Leu Glu Trp Ile
        35                  40                  45

Gly Trp Ile Phe Pro Gly Asp Asp Lys Thr Lys Tyr Asn Glu Lys Phe
    50                  55                  60

Lys Gly Arg Ala Thr Leu Thr Ser Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Lys Tyr Leu Asn Trp Asn Phe Asp Val Trp Gly Gln
            100                 105                 110

Gly Thr Thr Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

Asp Ile Val Leu Thr Gln Pro Gln Lys Phe Leu Ser Thr Ser Val Gly
1               5                   10                  15

Asp Arg Val Ser Val Thr Cys Lys Ala Asn Gln Asn Val Gly Thr Thr
            20                  25                  30

Leu Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys His Gln Tyr Thr Thr Tyr Pro Leu
                 85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic

<400> SEQUENCE: 19

Asp Ile Gln Leu Thr Gln Ser Pro Ser Phe Leu Ser Ala Ser Val Gly
 1               5                  10                  15

Asp Arg Val Thr Ile Thr Cys Lys Ala Asn Gln Asn Val Gly Thr Thr
                 20                  25                  30

Leu Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys His Gln Tyr Thr Thr Tyr Pro Leu
                 85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Gln Leu Thr Gln Ser Pro Ser Phe Leu Ser Ala Ser Val Gly
 1               5                  10                  15

Asp Arg Val Thr Ile Thr Cys Lys Ala Asn Gln Asn Val Gly Thr Thr
                 20                  25                  30

Leu Ala Trp Tyr Gln Gln Lys Pro Gly Lys Ala Pro Lys Ala Leu Ile
            35                  40                  45

Tyr Ser Ala Ser Tyr Arg Tyr Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys His Gln Tyr Thr Thr Tyr Pro Leu
                 85                  90                  95

Thr Phe Gly Gly Gly Thr Lys Val Glu Ile Lys
            100                 105

-continued

```
<210> SEQ ID NO 21
<211> LENGTH: 107
<212> TYPE: PRT
<213> ORGANISM: Artificial Sequence
<220> FEATURE:
<223> OTHER INFORMATION: Synthetic

<400> SEQUENCE: 21

Asp Ile Gln Leu Thr Gln Ser Pro Ser Phe Leu Ser Ala Ser Val Gly
1               5                   10                  15

Asp Arg Val Thr Ile Thr Cys Lys Ala Asn Gln Asn Val Gly Thr Thr
            20                  25                  30

Leu Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Thr Thr Tyr Pro Leu
                85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Gln Leu Thr Gln Ser Pro Ser Phe Leu Ser Ala Ser Val Gly
1               5                   10                  15

Asp Arg Val Thr Ile Thr Cys Lys Ala Asn Gln Asn Val Gly Thr Thr
            20                  25                  30

Leu Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Asp Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys His Gln Tyr Thr Thr Tyr Pro Leu
                85                  90                  95

Thr Phe Gly Gly Gly Thr Lys Val Glu Ile Lys
            100                 105

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Pro Tyr Ser Ile His
1               5

<210> SEQ ID NO 24
<211> LENGTH: 17
<212> TYPE: PRT
<213> ORGANISM: Artificial Sequence
```

```
<220> FEATURE:
<223> OTHER INFORMATION: Synthetic

<400> SEQUENCE: 24

Tyr Ile Asn Pro Ser Thr Gly Tyr Ile Glu Tyr Asn Gln His Phe Lys
1               5                   10                  15

Asp

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Gly Gly Asp Tyr Glu Gly Tyr Phe Asp Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Arg Leu Asn Glu Asn Ile Tyr Ser Phe Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Asn Ala Glu Thr Leu Ala Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Gln Gln His Tyr Gly Thr Pro Tyr Thr
1               5

<210> SEQ ID NO 29
<211> LENGTH: 119
<212> TYPE: PRT
<213> ORGANISM: Artificial Sequence
<220> FEATURE:
<223> OTHER INFORMATION: Synthetic

<400> SEQUENCE: 29

Gln Val Gln Leu Gln Gln Ser Ala Ala Glu Leu Val Arg Pro Gly Ala
1               5                   10                  15

Ser Val Lys Met Ser Cys Lys Ala Ser Gly Tyr Ile Phe Thr Pro Tyr
            20                  25                  30
```

```
Ser Ile His Trp Ile Lys Gln Arg Pro Gly Gln Gly Leu Glu Trp Ile
         35                  40                  45

Gly Tyr Ile Asn Pro Ser Thr Gly Tyr Ile Glu Tyr Asn Gln His Phe
 50                      55                  60

Lys Asp Arg Thr Thr Leu Thr Ala Asp Lys Ser Ser Ser Thr Ala Tyr
 65                  70                  75                  80

Met Gln Leu Arg Ser Leu Thr Ser Glu Asp Ser Ala Val Tyr Tyr Cys
                 85                  90                  95

Ala Arg Gly Gly Asp Tyr Glu Gly Tyr Phe Asp Tyr Trp Gly Gln Gly
             100                 105                 110

Thr Thr Leu Thr Val Ser Ser
            115

<210> SEQ ID NO 30
<211> LENGTH: 119
<212> TYPE: PRT
<213> ORGANISM: Artificial Sequence
<220> FEATURE:
<223> OTHER INFORMATION: Synthetic

<400> SEQUENCE: 30

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Pro Tyr
                 20                  25                  30

Ser Ile His Trp Val Arg Gln Ala Pro Gly Gln Gly Leu Glu Trp Met
         35                  40                  45

Gly Tyr Ile Asn Pro Ser Thr Gly Tyr Ile Glu Tyr Asn Gln His Phe
 50                      55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Asp Tyr Glu Gly Tyr Phe Asp Tyr Trp Gly Gln Gly
             100                 105                 110

Thr Thr Val Thr Val Ser Ser
            115

<210> SEQ ID NO 31
<211> LENGTH: 119
<212> TYPE: PRT
<213> ORGANISM: Artificial Sequence
<220> FEATURE:
<223> OTHER INFORMATION: Synthetic

<400> SEQUENCE: 31

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Pro Tyr
                 20                  25                  30

Ser Ile His Trp Val Arg Gln Ala Pro Gly Gln Gly Leu Glu Trp Met
         35                  40                  45

Gly Tyr Ile Asn Pro Ser Thr Gly Tyr Ile Glu Tyr Asn Gln His Phe
 50                      55                  60

Lys Asp Arg Val Thr Ile Thr Ala Asp Lys Ser Thr Ser Thr Ala Tyr
 65                  70                  75                  80

Met Glu Leu Arg Ser Leu Arg Ser Glu Asp Thr Ala Val Tyr Tyr Cys
                 85                  90                  95
```

Ala Arg Gly Gly Asp Tyr Glu Gly Tyr Phe Asp Tyr Trp Gly Gln Gly
            100                 105                 110

Thr Thr Val Thr Val Ser Ser
            115

<210> SEQ ID NO 32
<211> LENGTH: 119
<212> TYPE: PRT
<213> ORGANISM: Artificial Sequence
<220> FEATURE:
<223> OTHER INFORMATION: Synthetic

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ser Pro Tyr
            20                  25                  30

Ser Ile His Trp Val Arg Gln Ala Pro Gly Gln Gly Leu Glu Trp Met
        35                  40                  45

Gly Tyr Ile Asn Pro Ser Thr Gly Tyr Ile Glu Tyr Asn Gln His Phe
    50                  55                  60

Lys Asp Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Gly Gly Asp Tyr Glu Gly Tyr Phe Asp Tyr Trp Gly Gln Gly
            100                 105                 110

Thr Thr Val Thr Val Ser Ser
            115

<210> SEQ ID NO 33
<211> LENGTH: 119
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ser Pro Tyr
            20                  25                  30

Ser Ile His Trp Val Arg Gln Ala Pro Gly Gln Gly Leu Glu Trp Ile
        35                  40                  45

Gly Tyr Ile Asn Pro Ser Thr Gly Tyr Ile Glu Tyr Asn Gln His Phe
    50                  55                  60

Lys Asp Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Gly Gly Asp Tyr Glu Gly Tyr Phe Asp Tyr Trp Gly Gln Gly
            100                 105                 110

Thr Thr Val Thr Val Ser Ser
            115

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ser Pro Tyr
            20                  25                  30

Ser Ile His Trp Val Arg Gln Ala Pro Gly Gln Gly Leu Glu Trp Ile
        35                  40                  45

Gly Tyr Ile Asn Pro Ser Thr Gly Tyr Ile Glu Tyr Asn Gln His Phe
    50                  55                  60

Lys Asp Arg Thr Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Gly Gly Asp Tyr Glu Gly Tyr Phe Asp Tyr Trp Gly Gln Gly
            100                 105                 110

Thr Thr Val Thr Val Ser Ser
        115

<210> SEQ ID NO 35
<211> LENGTH: 119
<212> TYPE: PRT
<213> ORGANISM: Artificial Sequence
<220> FEATURE:
<223> OTHER INFORMATION: Synthetic

<400> SEQUENCE: 35

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Pro Tyr
            20                  25                  30

Ser Ile His Trp Val Arg Gln Ala Pro Gly Gln Gly Leu Glu Trp Ile
        35                  40                  45

Gly Tyr Ile Asn Pro Ser Thr Gly Tyr Ile Glu Tyr Asn Gln His Phe
    50                  55                  60

Lys Asp Arg Thr Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Gly Gly Asp Tyr Glu Gly Tyr Phe Asp Tyr Trp Gly Gln Gly
            100                 105                 110

Thr Thr Val Thr Val Ser Ser
        115

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Asp Ser Leu Ala Ser Val Gly
1               5                   10                  15

Glu Thr Val Thr Ile Thr Cys Arg Leu Asn Glu Asn Ile Tyr Ser Phe
            20                  25                  30

```
Leu Ala Trp Tyr Gln Gln Arg Gln Gly Lys Ser Pro Gln Leu Leu Val
                35                  40                  45

Tyr Asn Ala Glu Thr Leu Ala Glu Asp Val Pro Ser Arg Phe Ser Gly
 50                  55                  60

Ser Gly Ser Gly Thr Gln Phe Ser Leu Lys Ile Ser Ser Leu Gln Thr
 65                  70                  75                  80

Asp Asp Phe Gly Thr Tyr Tyr Cys Gln Gln His Tyr Gly Thr Pro Tyr
                85                  90                  95

Thr Phe Gly Gly Gly Thr Asn Leu Glu Ile Glu
                100                 105
```

<210> SEQ ID NO 37
<211> LENGTH: 107
<212> TYPE: PRT
<213> ORGANISM: Artificial Sequence
<220> FEATURE:
<223> OTHER INFORMATION: Synthetic

<400> SEQUENCE: 37

```
Asp Ile Gln Met Thr Gln Ser Pro Ser Ser Leu Ser Ala Ser Val Gly
 1               5                  10                  15

Asp Arg Val Thr Ile Thr Cys Arg Leu Asn Glu Asn Ile Tyr Ser Phe
                20                  25                  30

Leu Ala Trp Tyr Gln Gln Lys Pro Gly Lys Ala Pro Lys Leu Leu Ile
                35                  40                  45

Tyr Asn Ala Glu Thr Leu Ala Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Gly Thr Pro Tyr
                85                  90                  95

Thr Phe Gly Gly Gly Thr Lys Val Glu Ile Lys
                100                 105
```

<210> SEQ ID NO 38
<211> LENGTH: 107
<212> TYPE: PRT
<213> ORGANISM: Artificial Sequence
<220> FEATURE:
<223> OTHER INFORMATION: Synthetic

<400> SEQUENCE: 38

```
Asp Ile Gln Met Thr Gln Ser Pro Ser Ser Leu Ser Ala Ser Val Gly
 1               5                  10                  15

Asp Arg Val Thr Ile Thr Cys Arg Leu Asn Glu Asn Ile Tyr Ser Phe
                20                  25                  30

Leu Ala Trp Tyr Gln Gln Lys Pro Gly Lys Ala Pro Lys Leu Leu Val
                35                  40                  45

Tyr Asn Ala Glu Thr Leu Ala Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Gly Thr Pro Tyr
                85                  90                  95

Thr Phe Gly Gly Gly Thr Lys Val Glu Ile Lys
                100                 105
```

```
<210> SEQ ID NO 39
<211> LENGTH: 107
<212> TYPE: PRT
<213> ORGANISM: Artificial Sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Leu Asn Glu Asn Ile Tyr Ser Phe
            20                  25                  30

Leu Ala Trp Tyr Gln Gln Lys Pro Gly Lys Ala Pro Lys Leu Leu Val
        35                  40                  45

Tyr Asn Ala Glu Thr Leu Ala Glu Asp Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gly Thr Pro Tyr
                85                  90                  95

Thr Phe Gly Gly Gly Thr Lys Val Glu Ile Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Leu Asn Glu Asn Ile Tyr Ser Phe
            20                  25                  30

Leu Ala Trp Tyr Gln Gln Lys Pro Gly Lys Ala Pro Lys Leu Leu Val
        35                  40                  45

Tyr Asn Ala Glu Thr Leu Ala Glu Asp Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Gln His Tyr Gly Thr Pro Tyr
                85                  90                  95

Thr Phe Gly Gly Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Synthetic

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Leu Asn Glu Asn Ile Tyr Ser Phe
            20                  25                  30
```

```
Leu Ala Trp Tyr Gln Gln Lys Pro Gly Lys Ser Pro Lys Leu Leu Val
        35                  40                  45

Tyr Asn Ala Glu Thr Leu Ala Glu Asp Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln Gln His Tyr Gly Thr Pro Tyr
                85                  90                  95

Thr Phe Gly Gly Gly Thr Lys Val Glu Ile Lys
            100                 105

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Asp Tyr Thr Leu Thr
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Gly Tyr Thr Phe Thr
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic

<400> SEQUENCE: 44

Gly Tyr Ile Phe Thr
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Gly Tyr Ile Phe Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 46

Gly Gly Thr Phe Ser
1               5
```